US 7,875,014 B2

(12) United States Patent
Hendren et al.

(10) Patent No.: US 7,875,014 B2
(45) Date of Patent: Jan. 25, 2011

(54) ABSORBENT GARMENT HAVING A GARMENT SHELL

(75) Inventors: Cynthia H. Hendren, Winneconne, WI (US); Kathleen I. Ratliff, Neenah, WI (US); Erica L. Mullen, Oshkosh, WI (US); Maria E. de Leon, Hortonville, WI (US); Susan M. Weyenberg, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1174 days.

(21) Appl. No.: 11/118,046

(22) Filed: Apr. 29, 2005

(65) Prior Publication Data

US 2006/0116656 A1 Jun. 1, 2006

Related U.S. Application Data

(63) Continuation-in-part of application No. 10/736,069, filed on Dec. 15, 2003, now Pat. No. 7,686,796.

(51) Int. Cl.
 *A61F 13/15* (2006.01)

(52) U.S. Cl. ........................................ 604/396; 604/393

(58) Field of Classification Search ............ 604/385.14, 604/393–396
See application file for complete search history.

(56) References Cited

U.S. PATENT DOCUMENTS

| | | | |
|---|---|---|---|
| 1,664,298 A | 3/1928 | Katz | |
| 1,971,558 A | 8/1934 | Goodman | |
| 2,030,306 A | 2/1936 | Lain | |
| 2,088,302 A | 1/1937 | Mckeever | |
| 2,252,019 A | 8/1941 | Meinecke et al. | |
| 2,450,789 A | 10/1948 | Frieman | |
| 2,566,325 A | 9/1951 | Ganz | |
| 2,675,806 A | 4/1954 | Bram | |
| 2,711,735 A | 1/1955 | Sabo | |
| 2,838,047 A | 6/1958 | Sidnell | |
| 2,842,129 A | 7/1958 | Ernstorff | |
| 2,859,752 A | 11/1958 | Haber | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |

(Continued)

FOREIGN PATENT DOCUMENTS

AT        168 478        6/1951

(Continued)

OTHER PUBLICATIONS

US 5,915,536, 06/1999, Alberts et al. (withdrawn)

*Primary Examiner*—Michele Kidwell
(74) *Attorney, Agent, or Firm*—H. Michael Kubicki

(57) ABSTRACT

A disposable absorbent garment for wear about a wearer's waist includes a garment shell and an absorbent assembly constructed to take in and retain body exudates released by the wearer, the absorbent assembly including an inner waist band. The absorbent assembly may be permanently detached from the garment shell. The garment shell has limited attachment to the absorbent assembly at front and rear attachment zones. The inner waist belt provides tension on each side of the absorbent assembly to provide effective coverage of the wearer.

19 Claims, 20 Drawing Sheets

U.S. PATENT DOCUMENTS

| | | |
|---|---|---|
| 3,542,615 A | 11/1970 | Dobo et al. |
| 3,648,699 A | 3/1972 | Anderson et al. |
| 3,678,516 A | 7/1972 | Backer |
| 3,692,618 A | 9/1972 | Dorschner et al. |
| 3,714,946 A | 2/1973 | Rudes |
| 3,802,817 A | 4/1974 | Matsuki et al. |
| 3,844,282 A | 10/1974 | King |
| 3,849,241 A | 11/1974 | Butin et al. |
| 3,859,667 A | 1/1975 | Roy |
| 4,114,621 A | 9/1978 | Mims, Jr. |
| 4,205,679 A | 6/1980 | Repke et al. |
| 4,231,358 A | 11/1980 | Atchison |
| 4,244,368 A | 1/1981 | Caradonna |
| 4,280,230 A | 7/1981 | Lafleur |
| 4,310,929 A | 1/1982 | Finlay |
| 4,338,939 A | 7/1982 | Daville |
| 4,340,563 A | 7/1982 | Appel et al. |
| 4,490,148 A | 12/1984 | Beckstrom |
| 4,555,245 A | 11/1985 | Armbruster |
| 4,644,945 A | 2/1987 | Thorner |
| 4,663,220 A | 5/1987 | Wisneski et al. |
| 4,664,663 A | 5/1987 | Brier |
| 4,671,793 A | 6/1987 | Hults et al. |
| 4,704,116 A | 11/1987 | Enloe |
| 4,745,636 A | 5/1988 | Lunt |
| 4,870,958 A | 10/1989 | Webster |
| 4,872,221 A | 10/1989 | Stone, III |
| 4,892,598 A | 1/1990 | Stevens et al. |
| 4,940,464 A | 7/1990 | Van Gompel et al. |
| 4,955,880 A | 9/1990 | Rodriquez |
| 4,964,860 A | 10/1990 | Gipson et al. |
| 4,965,122 A | 10/1990 | Morman |
| 4,981,747 A | 1/1991 | Morman |
| 5,046,272 A | 9/1991 | Vogt et al. |
| 5,052,058 A | 10/1991 | Mueller |
| 5,067,178 A | 11/1991 | Katchka |
| 5,103,505 A | 4/1992 | Llorens |
| 5,104,116 A | 4/1992 | Pohjola |
| 5,108,385 A | 4/1992 | Snyder |
| 5,135,522 A | 8/1992 | Fahrenkrug et al. |
| 5,204,997 A | 4/1993 | Suzuki et al. |
| 5,210,882 A | 5/1993 | Moretz et al. |
| 5,212,839 A | 5/1993 | Sliman et al. |
| 5,213,881 A | 5/1993 | Timmons et al. |
| 5,217,782 A | 6/1993 | Moretz et al. |
| 5,224,405 A | 7/1993 | Pohjola |
| 5,226,992 A | 7/1993 | Morman |
| D341,243 S | 11/1993 | Costella et al. |
| 5,297,296 A | 3/1994 | Moretz et al. |
| 5,303,424 A | 4/1994 | Cromartie |
| 5,306,536 A | 4/1994 | Moretz et al. |
| 5,315,716 A | 5/1994 | Baum |
| 5,315,717 A | 5/1994 | Moretz et al. |
| 5,336,545 A | 8/1994 | Morman |
| 5,364,382 A | 11/1994 | Latimer et al. |
| 5,370,634 A | 12/1994 | Ando et al. |
| 5,379,462 A | 1/1995 | Morgan et al. |
| 5,389,095 A | 2/1995 | Suzuki et al. |
| 5,435,014 A | 7/1995 | Moretz et al. |
| 5,445,628 A | 8/1995 | Gipson et al. |
| 5,486,166 A | 1/1996 | Bishop et al. |
| 5,490,846 A | 2/1996 | Ellis et al. |
| 5,549,593 A | 8/1996 | Ygge et al. |
| D377,557 S | 1/1997 | Jagger |
| 5,649,913 A | 7/1997 | Cohen |
| D382,386 S | 8/1997 | Malone |
| 5,669,902 A | 9/1997 | Sivilich |
| 5,690,626 A | 11/1997 | Suzuki et al. |
| 5,690,627 A | 11/1997 | Clear et al. |
| 5,700,256 A | 12/1997 | Yamamoto et al. |
| 5,718,003 A | 2/1998 | Gwinn |
| 5,766,389 A | 6/1998 | Brandon et al. |
| 5,772,649 A | 6/1998 | Siudzinski |
| 5,790,983 A | 8/1998 | Rosch et al. |
| 5,827,260 A | 10/1998 | Suzuki et al. |
| 5,853,405 A | 12/1998 | Suprise |
| 5,858,012 A | 1/1999 | Yamaki et al. |
| 5,858,515 A | 1/1999 | Stokes et al. |
| 5,876,394 A | 3/1999 | Rosch et al. |
| 5,891,122 A | 4/1999 | Coates |
| D408,964 S | 5/1999 | Hernandez |
| 5,906,604 A | 5/1999 | Ronnberg et al. |
| 5,953,754 A | 9/1999 | Rosch et al. |
| 5,978,971 A | 11/1999 | Wald |
| D417,940 S | 12/1999 | Coates et al. |
| 6,009,558 A | 1/2000 | Rosch et al. |
| 6,010,586 A | 1/2000 | Suprise |
| 6,013,066 A | 1/2000 | Samuelsson |
| 6,018,822 A | 2/2000 | Hernandez |
| 6,098,557 A | 8/2000 | Couillard et al. |
| 6,105,171 A | 8/2000 | Niedermeyer |
| 6,108,823 A | 8/2000 | Danes |
| 6,115,847 A | 9/2000 | Rosch et al. |
| 6,142,983 A | 11/2000 | Suprise et al. |
| 6,145,132 A | 11/2000 | Towner |
| 6,149,637 A | 11/2000 | Allen et al. |
| 6,168,585 B1 | 1/2001 | Cesco-Cancian |
| 6,174,303 B1 | 1/2001 | Suprise et al. |
| 6,192,521 B1 | 2/2001 | Alberts et al. |
| 6,197,012 B1 | 3/2001 | Mishima et al. |
| 6,293,934 B1 | 9/2001 | Kumasaka |
| 6,293,936 B1 | 9/2001 | Otsubo |
| 6,293,937 B2 | 9/2001 | Matsushita et al. |
| 6,295,651 B1 | 10/2001 | Kang |
| 6,312,420 B1 | 11/2001 | Sasaki et al. |
| 6,342,050 B1 | 1/2002 | Rönnberg et al. |
| 6,358,350 B1 | 3/2002 | Glaug et al. |
| 6,368,312 B1 | 4/2002 | Otsubo |
| D456,995 S | 5/2002 | Baker |
| 6,419,665 B1 | 7/2002 | Cohen |
| 6,423,043 B1 | 7/2002 | Gustafsson |
| 6,425,140 B1 | 7/2002 | Vitches |
| 6,458,116 B1 | 10/2002 | Matsushita |
| 6,475,201 B2 | 11/2002 | Saito et al. |
| 6,475,205 B2 | 11/2002 | Shimada et al. |
| 6,487,727 B1 | 12/2002 | Harsant |
| 6,516,473 B2 | 2/2003 | Saito |
| 6,539,554 B1 | 4/2003 | Portela |
| 6,547,774 B2 | 4/2003 | Ono et al. |
| 6,550,288 B2 | 4/2003 | Browder, Jr. et al. |
| 6,558,364 B1 | 5/2003 | Santa Cruz et al. |
| 6,585,840 B2 | 7/2003 | Rabe et al. |
| 6,595,973 B2 | 7/2003 | Sugito |
| 6,613,034 B2 | 9/2003 | Nozaki et al. |
| 6,635,042 B2 | 10/2003 | Kumasaka |
| 6,648,868 B2 | 11/2003 | Sayama et al. |
| 6,651,463 B2 | 11/2003 | Bonnin |
| 6,666,851 B2 | 12/2003 | Otsubo et al. |
| 6,676,647 B2 | 1/2004 | Shimada et al. |
| 6,761,712 B2 | 7/2004 | Otsubo et al. |
| 6,793,650 B2 | 9/2004 | Weber |
| 6,964,238 B2 | 11/2005 | Mortell et al. |
| 7,192,500 B2 | 3/2007 | Allen |
| 2002/0004655 A1 | 1/2002 | Shimada et al. |
| 2002/0035747 A1 | 3/2002 | Kusibojoska et al. |
| 2002/0123732 A1 | 9/2002 | Koyama et al. |
| 2002/0177825 A1 | 11/2002 | Scovel |
| 2003/0023219 A1 | 1/2003 | Nakaoka |
| 2003/0088955 A1 | 5/2003 | Bridges |
| 2003/0115660 A1 | 6/2003 | Hopkins |
| 2003/0216705 A1 | 11/2003 | Coates |
| 2003/0217407 A1 | 11/2003 | Andrews-Jones |
| 2003/0217803 A1 | 11/2003 | Hermansson et al. |
| 2003/0229329 A1 | 12/2003 | Mercier et al. |

| | | | | | | |
|---|---|---|---|---|---|---|
| 2004/0060648 | A1 | 4/2004 | Thorson et al. | EP | 1 247 506 A2 | 10/2002 |
| 2004/0082932 | A1 | 4/2004 | Lauritzen | EP | 1 247 507 A2 | 10/2002 |
| 2004/0098791 | A1 | 5/2004 | Faulks | EP | 1 260 206 A2 | 11/2002 |
| 2004/0102746 | A1 | 5/2004 | Mortell et al. | EP | 1 504 738 A2 | 2/2005 |
| 2004/0107481 | A1 | 6/2004 | Mortell et al. | FR | 1 276 791 A | 11/1961 |
| 2004/0108043 | A1 | 6/2004 | Otsubo | GB | 701081 A | 12/1953 |
| 2004/0116881 | A1 | 6/2004 | Nordness et al. | GB | 774712 A | 5/1957 |
| 2005/0125879 | A1 | 6/2005 | Yang et al. | GB | 1 342 022 A | 12/1973 |
| 2005/0131377 | A1 | 6/2005 | Franke et al. | GB | 2 196 525 | 5/1988 |
| 2005/0131381 | A1 | 6/2005 | Kuen et al. | GB | 2 208 263 A | 3/1989 |
| 2005/0131382 | A1 | 6/2005 | Brud et al. | GB | 2 269 978 A | 3/1994 |
| 2005/0148980 | A1 | 7/2005 | Fitton | GB | 2 269 998 A | 3/1994 |
| 2006/0148359 | A1 | 7/2006 | Van Gompel et al. | GB | 2 269 999 A | 3/1994 |

FOREIGN PATENT DOCUMENTS

| | | | | | |
|---|---|---|---|---|---|
| | | | GB | 2 327 859 A | 2/1999 |
| AU | 94/80371 B | 4/1995 | JP | 2000-355801 A | 12/2000 |
| DE | 435 579 | 2/1927 | JP | 2001-172802 A | 6/2001 |
| DE | 839 244 | 5/1952 | JP | 2001-204762 A | 7/2001 |
| EP | 0 400 895 A1 | 12/1990 | JP | 2001-238909 A | 9/2001 |
| EP | 0 217 032 B1 | 2/1992 | JP | 2001-248002 A | 9/2001 |
| EP | 0 549 988 B1 | 6/1998 | JP | 2001-254202 A | 9/2001 |
| EP | 0 904 758 A2 | 3/1999 | JP | 2001-309946 A | 11/2001 |
| EP | 0 911 006 A1 | 4/1999 | JP | 2002-035022 A | 2/2002 |
| EP | 1 048 231 A1 | 11/2000 | WO | WO 95/18589 A1 | 7/1995 |
| EP | 1 060 677 A1 | 12/2000 | WO | 96 03950 * | 2/1996 |
| EP | 1 092 355 A1 | 4/2001 | WO | WO 96/03949 A1 | 2/1996 |
| EP | 1 108 371 A1 | 6/2001 | WO | WO 96/03950 A1 | 2/1996 |
| EP | 1 108 372 A1 | 6/2001 | WO | WO 97/24091 A1 | 7/1997 |
| EP | 1 108 373 A1 | 6/2001 | WO | WO 98/53785 A1 | 12/1998 |
| EP | 1 159 883 A1 | 12/2001 | WO | WO 99/33421 A1 | 7/1999 |
| EP | 1 166 730 A2 | 1/2002 | WO | WO 00/37009 A2 | 6/2000 |
| EP | 1 179 302 A2 | 2/2002 | WO | WO 01/88245 A2 | 11/2001 |
| EP | 1 184 012 A1 | 3/2002 | WO | WO 02/067833 A1 | 9/2002 |
| EP | 1 188 427 A1 | 3/2002 | WO | WO 2004/073430 A2 | 9/2004 |
| EP | 1 219 273 A2 | 7/2002 | | | |

* cited by examiner

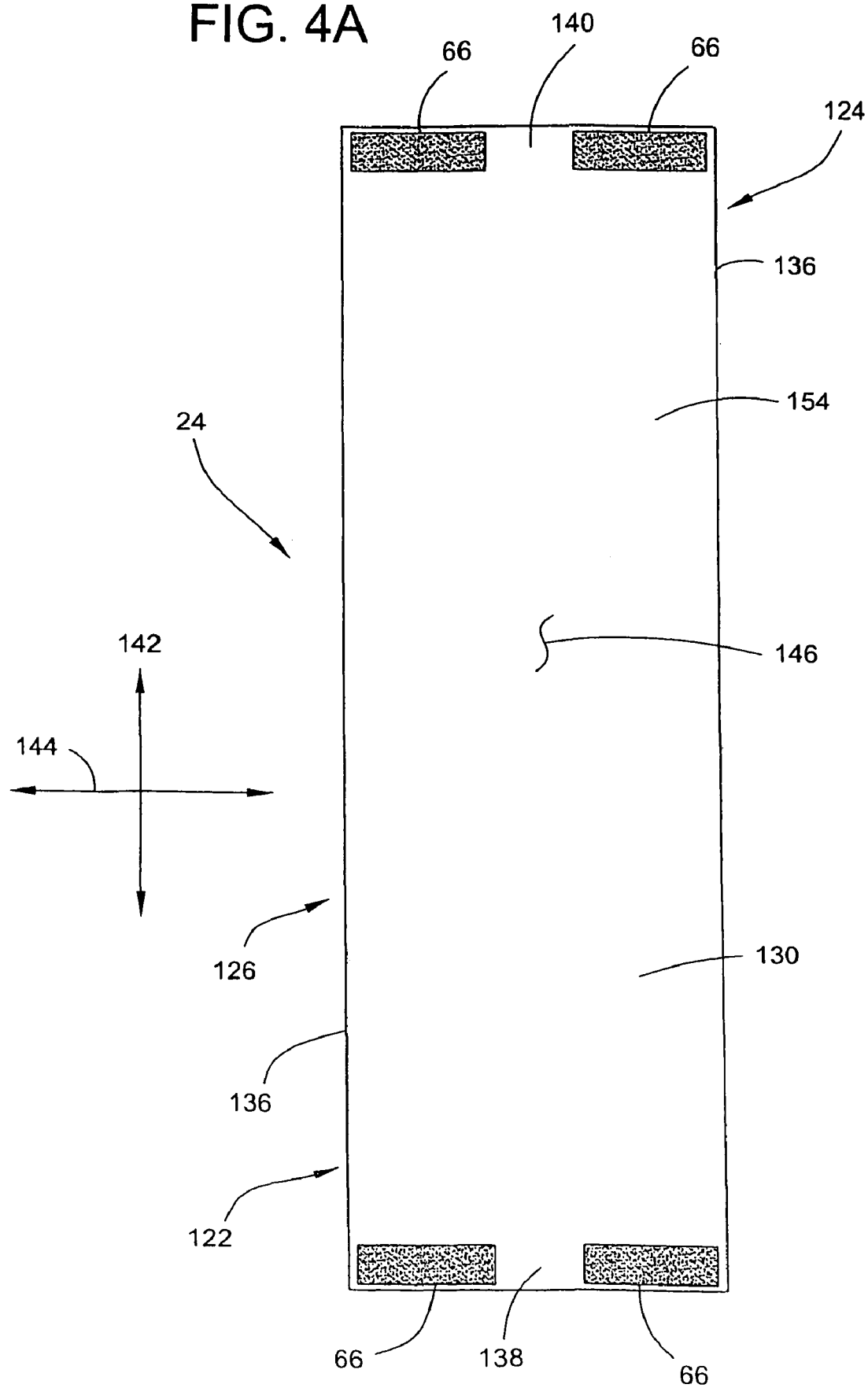

ABSORBENT GARMENT HAVING A GARMENT SHELL

RELATED APPLICATION

This application is a continuation-in-part of U.S. patent application Ser. No. 10/736,069, filed Dec. 15, 2003 now U.S. Pat. No. 7,686,796. The disclosure of the prior application is incorporated herein by reference.

BACKGROUND OF THE INVENTION

This invention relates generally to absorbent garments, and more particularly to such absorbent garments having the appearance of conventional clothing.

Personal wear garments and other articles find widespread use as personal care products including, without limitation, diapers, children's toilet training pants, adult incontinence garments, sanitary napkins and the like, as well as surgical bandages and sponges. The primary purpose of such articles is to take in and retain body exudates released by a wearer to thereby prevent soiling of the wearer's or caregiver's clothing. Certain absorbent articles are suitably disposable in that they are intended to be discarded after a limited period of use, i.e., the articles are not intended to be laundered or otherwise restored for reuse. Disposable absorbent articles typically comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

In particular absorbent articles, such as children's training pants, various attempts have been made to make the articles more visually appealing, such as by applying certain graphics or other features which make the articles appear more like conventional clothing, and more particularly like conventional undergarments. Training pants represent an intermediate stage for a child between using diapers and using cloth underpants. By making the training pants more closely resemble the undergarments or other clothing that an older sibling or parent wears, it is believed that children ready for toilet training will be more amenable to wearing the training pants. Other absorbent pants-type articles are worn by older children that still experience nighttime incontinence and by adults who experience periodic incontinence. These persons are typically more sensitive to issues of discretion and therefore desire some way to conceal the fact that they are wearing absorbent pants.

One drawback to simply improving the external appearance of existing absorbent pants is that the entire pants must still be discarded after use. As a result, additional features which are added to entice children to wear the pants or otherwise conceal the absorbent look of the pants add further costs to making and using the pants. Moreover, clothes must still be worn over the absorbent pants, which can be uncomfortable and results in a rather bulky appearance. Also, to inhibit the leakage of exudates from absorbent articles such as training pants or other absorbent pants, it is important that the article fit generally snug against the wearer's body. For example, conventional training pants are constructed to provide a generally elastic fit about the wearer's waist and about the wearer's legs to inhibit leakage from the pants. However, many conventional garments that are worn about one's waist, such as shorts, skirts, skorts, boxer shorts, swim trunks and the like, all have a more loose fitting appearance, particularly about the legs of the wearer.

As a result, there has remained a need for improved disposable absorbent garments having the appearance of conventional clothing and a desirable fit.

SUMMARY OF THE INVENTION

In general, one version of the present invention concerning a disposable absorbent garment for wear about a wearer's waist includes a garment shell and an absorbent assembly. The garment shell is configured for encircling the wearer's waist, and has a front waist region with a front waist end, and a back waist region with a back waist end. The garment shell includes a front panel assembly with laterally opposite side margins, and a back panel assembly with laterally opposite side margins. The garment shell further includes a waist band located at the front and back waist end thereof. The absorbent assembly, constructed to take in and retain body exudates released by the wearer, is disposed within the garment shell. The absorbent assembly has a front waist region in juxtaposed relation with the front waist region of the garment shell, and a back waist region in juxtaposed relation with the back waist region of the garment shell. The absorbent assembly further includes a crotch region extending longitudinally between and interconnecting the front waist region and the back waist region. A front waist end of the absorbent assembly has a front attachment zone, and a back waist end of the absorbent assembly has a rear attachment zone. The front attachment zone is permanently attached to the front waist region of the garment shell, and the rear attachment zone is permanently attached to the back waist region of the garment shell. The absorbent assembly has laterally opposite outer edges defining a width thereof. The front attachment zone and the rear attachment zone each have a width that is about 1 percent to about 70 percent of the width of the absorbent assembly.

In another version of the present invention, the garment shell includes a shell waist band comprising at least one elastic member operatively attached to at least the garment shell front waist end or the garment shell back waist end, and the absorbent assembly includes an inner waist band for supporting the absorbent assembly around the wearer's waist, the inner waist band attached to the front waist and the back waist end of the absorbent assembly. The absorbent assembly has laterally opposite outer edges defining a width thereof, and the front attachment zone and the rear attachment zone each have a width that is about 5 percent to about 60 percent of the width of the absorbent assembly. The shell waist band is permanently and operatively attached to the inner waist band at the front and rear attachment zones.

In yet another version of the present invention, the garment shell includes a shell waist band comprising at least one elastic member operatively attached to at least the garment shell front waist end or the garment shell back waist end, and the absorbent assembly includes an inner band for supporting the absorbent assembly around the wearer's torso, the inner band-attached to laterally-opposite outer edges the absorbent assembly. The absorbent assembly laterally opposite outer edges define a width thereof, and the front attachment zone and the rear attachment zone each have a width that is about 1 percent to about 95 percent of the width of the absorbent assembly. The shell waist band is permanently and operatively attached to the absorbent assembly at the front and rear attachment zones. The absorbent garment has at least one outer leg opening and a pair of inner leg openings separate from the at least one leg opening and disposed within the garment shell. The absorbent assembly at least in part defines the inner leg openings of the absorbent garment, and the garment shell defines the at least one outer leg opening of the absorbent garment. The absorbent assembly is configured to provide an elastic fit of the absorbent assembly against the wearer's legs at the inner leg openings of the absorbent garment, and the garment shell being configured to generally hang loose about the wearer's legs at the at least one outer leg opening of the absorbent garment.

It is understood that both the foregoing general description and the following detailed description are exemplary and are intended to provide further explanation of the invention claimed. The accompanying drawings, which are incorporated in and constitute part of this specification, are included to illustrate and provide a further understanding of the article of the present invention. Together with the description, the drawings serve to explain the various aspects of the invention.

DEFINITIONS

Within the context of this specification, each term or phrase below will include the following meaning or meanings.

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Longitudinal," and "transverse" or "lateral," have their customary meaning, as indicated by the longitudinal and transverse axes depicted in FIG. 4 and respectively designated 142 and 144.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers may be found in, for example, U.S. Pat. No. 5,213,881, entitled "A Nonwoven Web With Improved Barrier Properties".

"Non-woven" as used in reference to a material, web or fabric refers to such a material, web or fabric having a structure of individual fibers or threads that are interlaid, but not in a regular or identifiable manner as in a knitted fabric. Non-woven materials, fabrics or webs have been formed from many processes such as, for example, meltblowing processes, spunbonding processes, air laying processes, and bonded carded web processes. The basis weight of non-wovens is usually expressed in ounces of material per square yard (osy) or grams per square meter (gsm) and the fiber diameters are usually expressed in microns. (Note: to convert from osy to gsm, multiply osy by 33.91.).

"Operatively joined," with reference to the attachment of an elastic member to another element, means that the elastic member when attached to or connected to the element, or treated with heat or chemicals, by stretching, mechanical straining or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated by reference in its entirety and in a manner consistent with the present document. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Stretch bonded" refers to an elastic member being bonded to another member while the elastic member is extended at least about 25 percent of its relaxed length. More suitably, the term "stretch bonded" refers to the situation wherein the elastic member is extended at least about 100 percent, and even more suitably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Tacked" refers to the temporary joining, adhering, connecting, bonding or the like of two elements. Once the two elements have been separated, they remain separated.

"Thermoplastic" describes a material which softens when exposed to heat and which substantially returns to a non-softened condition when cooled to room temperature.

These terms may be further defined with additional language in the remaining portions of the specification.

BRIEF DESCRIPTION OF THE DRAWINGS

FIG. 4a is a plan view similar to FIG. 4, but showing the surface of the absorbent that faces away from the wearer of the absorbent garment;

Corresponding reference characters indicate corresponding parts throughout the drawings.

DETAILED DESCRIPTION

Figure 1:
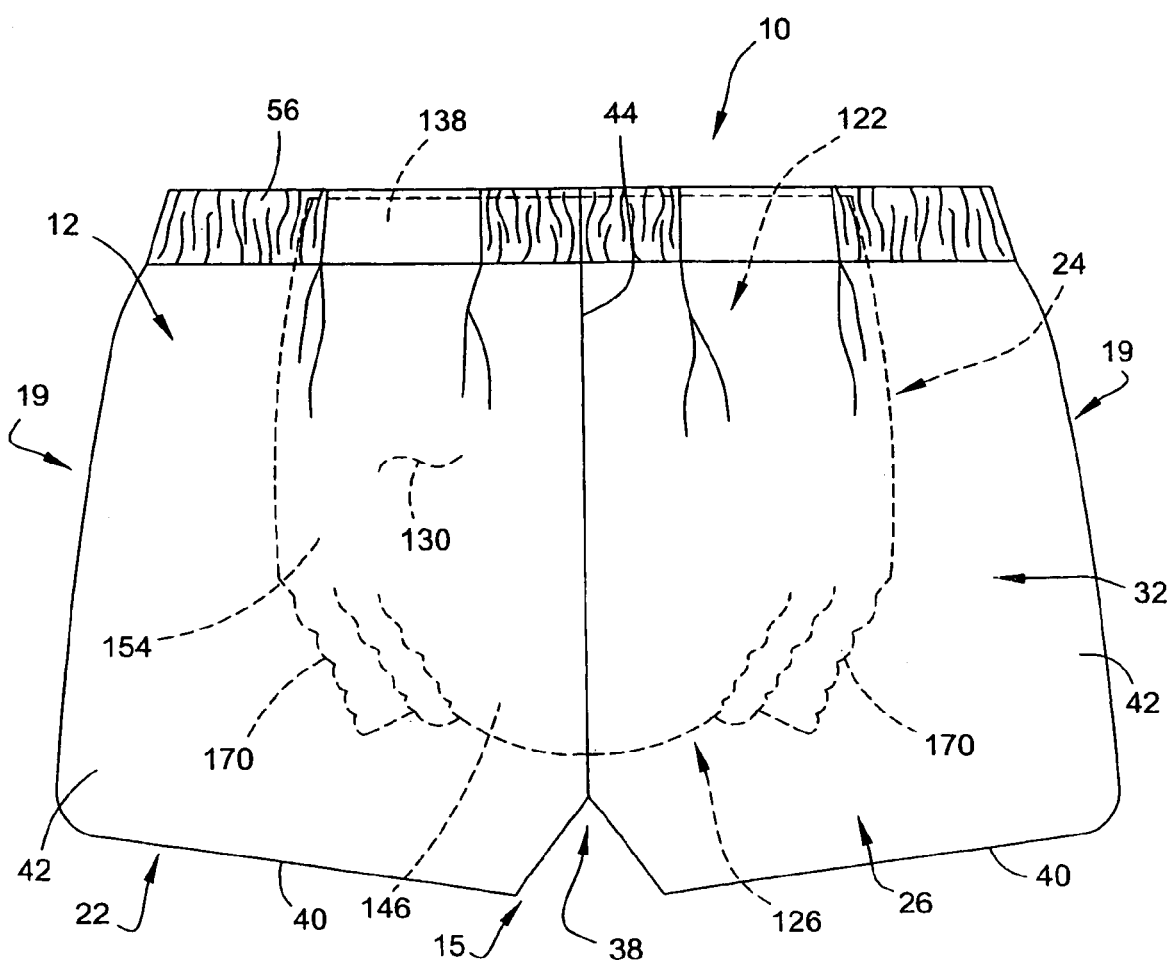
FIG. 1 is a front elevation of an absorbent garment according to one embodiment of the present invention.
Figure 2:
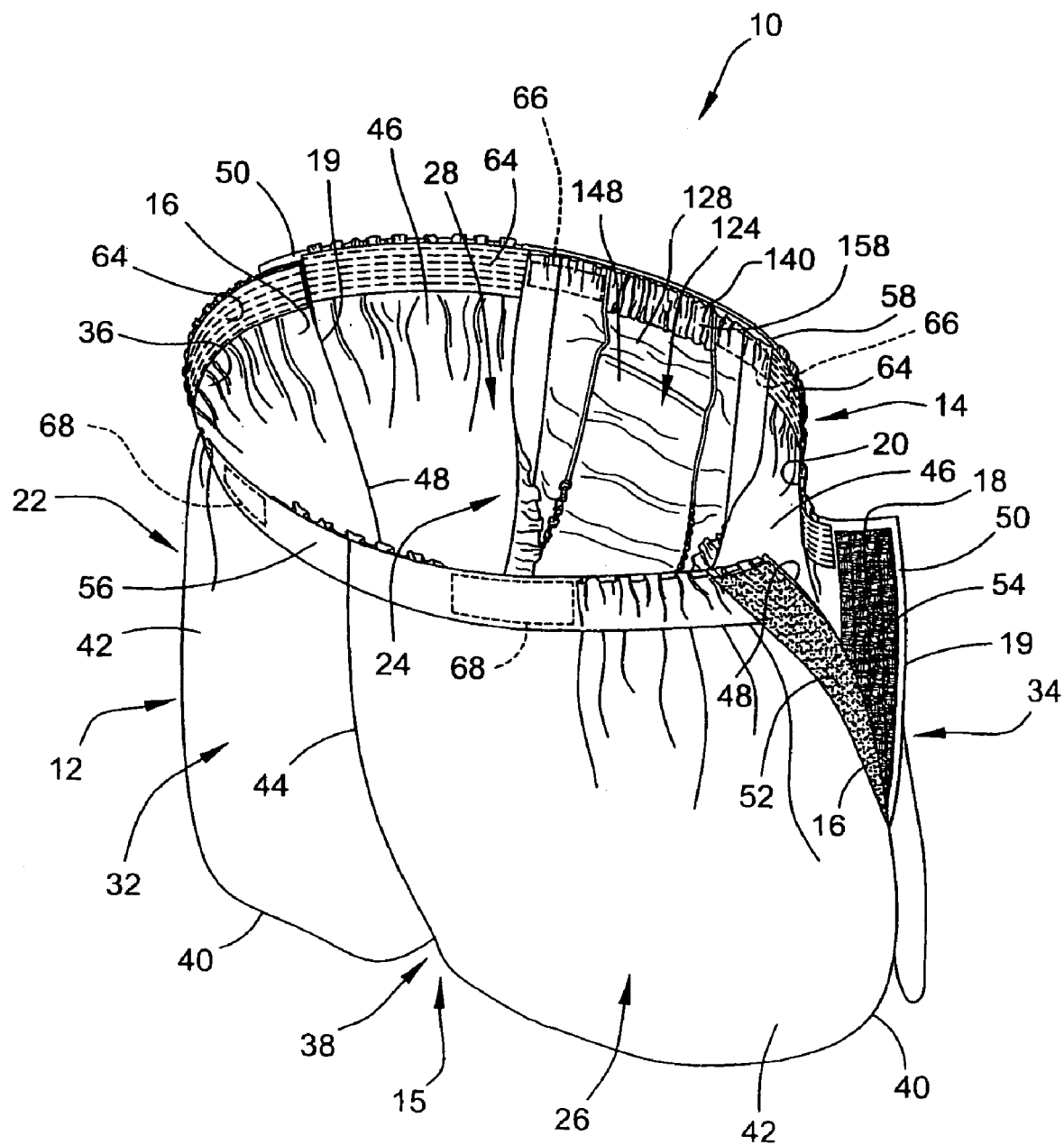
FIG. 2 is a perspective of the absorbent garment of FIG. 1 with a side seam of the absorbent garment shown in an unfastened condition.

Referring now to the drawings, and in particular to FIGS. 1 and 2, an absorbent garment according to one embodiment of the present invention is indicated in its entirety by the reference numeral 10. The absorbent garment 10 is configured to be worn on a wearer's waist and generally has a front waist region, indicated generally at 12, a back waist region, indicated generally at 14 and a crotch region, indicated generally at 15. The front and back waist regions 12, 14 have respective side margins 16, 18 which are attached to each other along side seams 19 of the garment to form a three dimensional configuration of the garment during wear and having a waist opening, generally indicated at 20. As used herein, the term "seam" is intended to refer to a region along which two components are overlapped or otherwise in abutment with each other and may or may not be attached to each other.

As described further herein, the absorbent garment is suitably configured to resemble conventional clothing such as shorts (e.g., boxer shorts, gym shorts, running shorts, etc.), skirts, skorts (i.e., a combination of a skirt and a pair of shorts), swim trunks and the like, while providing the functions of conventional absorbent articles, such as taking in and retaining body exudates released by the wearer. The absorbent garment 10 comprises a garment shell, generally indicated at 22 and constructed to provide the desired resemblance of the garment to conventional clothing, and an absorbent assembly, generally indicated at 24, disposed within and releasably attached to the garment shell and constructed to take in and retain body exudates released by the wearer.

With particular reference to FIGS. 1 and 2, the garment shell 22 comprises a front panel assembly, which is generally indicated at 26, having laterally opposite side margins 48 and a back panel assembly, which is generally indicated at 28 in FIG. 2, having laterally opposite side margins 50. In the illustrated embodiment, the side margins 48 of the front panel assembly 26 broadly define the front side margins 16 of the absorbent garment 10 and the side margins 50 of the back panel assembly 28 broadly define the back side margins 18 of the absorbent garment. As will be described in further detail later herein, the side margins 48, 50 of the front and back panel assemblies 26, 28 of the garment shell 22 are overlapped and attached to each other to broadly define the side seams 19 of the absorbent garment 10, and to define the three-dimensional configuration of the garment shell during wear.

In its three-dimensional configuration as shown in FIGS. 1 and 2, the garment shell 22 has a front waist region 32 which at least in part defines the front waist region 12 of the absorbent garment 10, a back waist region 34 which at least in part defines the back waist region 14 of the absorbent garment, and front and back waist ends, designated 56 and 58, respectively, which together generally define a waist opening 36 of the garment shell. In the illustrated embodiment, the garment shell 22 is configured to resemble a pair of shorts and thus further has a crotch region 38 extending longitudinally between and interconnecting the front waist region 32 and the back waist region 34 of the garment shell. The crotch region 38 of the garment shell 22 at least in part defines the crotch region 15 of the absorbent garment 10, and also in part defines leg openings 40 of the garment shell (broadly referred to herein as outer leg openings of the absorbent garment). However, it is understood that the crotch region 38 of the garment shell 22 may be omitted (so that the crotch region 15 of the absorbent garment 10 is defined solely by the absorbent assembly 24 as described later herein), such as where the garment shell is intended to resemble a skirt (in which case only one leg opening 40 of the garment shell is provided to accommodate both legs of the wearer), without departing from the scope of this invention.

The front panel assembly 26 of the garment shell 22 comprises a pair of panel members 42 which are permanently attached to each other, such as by ultrasonic bonding, thermal bonding, adhesive bonding, stitching or other conventional attachment technique, along a central seam 44 extending longitudinally from the front waist region 32 to the crotch region 38 of the garment shell. The back panel assembly 28 comprises a pair of panel members 46 configured and permanently attached to each other in a manner similar to the panel members 42 of the front panel assembly 26 along a central seam 47 (FIG. 3) extending longitudinally from the back waist region 34 to the crotch region 38 of the garment shell 22. It is understood, however, that each of the front and back panel assemblies 26, 28 may be constructed of a single panel member (e.g., of unitary construction) without departing from the scope of this invention. Alternatively, the front and back panel members 42, 46 on one side of the garment shell 22 may be formed integrally at the crotch region 38 thereof so that no attachment of the panel members is necessary at the leg openings.

The panel members 42, 46 of the front and back panel assemblies 26, 28 of the garment shell 22 can be constructed of any suitable material, and more suitably a material that provides a generally cloth-like texture. The panel members 42, 46 are also suitably constructed of a material which is relatively durable so that the garment shell 22 can be re-used through multiple replacements of the absorbent assembly. It is also contemplated that the panel members 42, 46 may, but need not necessarily be, constructed of a material suitable for laundering to permit laundering of the garment shell. As an example, the panel members 42, 46 may be constructed from natural and/or synthetic sources and may be constructed in any suitable manner including, but not limited to nonwovens such as spunbond, meltblown, spunbond film laminates, bonded carded web, spunlace, hydroentangled, and needlepunched; knit fabrics such as stretch knit, fleece knit, herringbone knit, jersey knit, raschel knit; and woven fabrics such as broadcloth, twill, percale, poplin, muslin, cambric, chino, flannel, silks and woolens. The panel members 42, 46 are suitably liquid permeable, although it is understood that the panel members may be liquid impermeable without departing from the scope of this invention.

Figure 3:
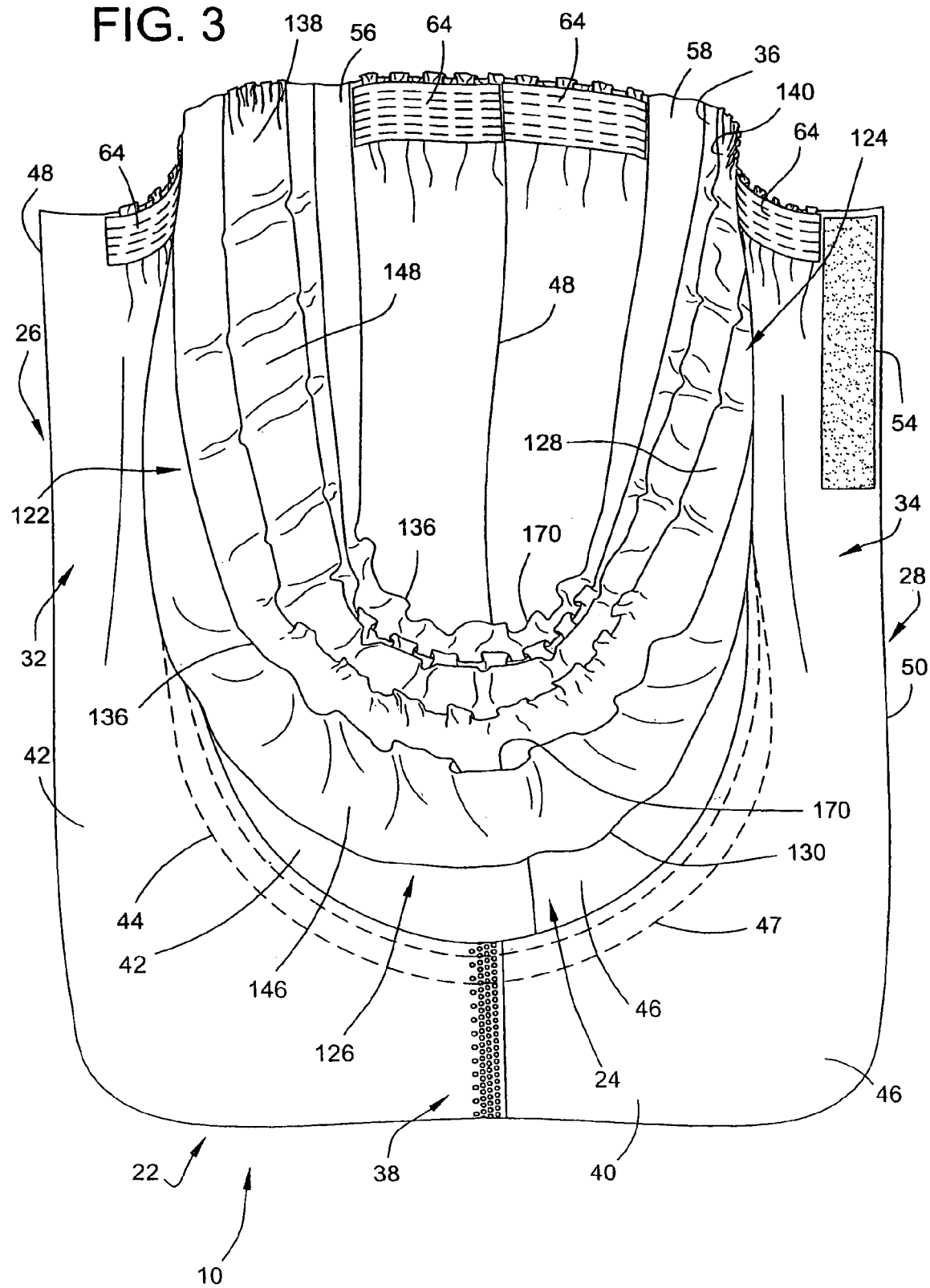
FIG. 3 is a side elevation of the absorbent garment of FIG. 1 with a side seam of the absorbent garment shown in an unfastened condition.

With particular reference to FIGS. 2 and 3, the front and back panel assemblies 26, 28 of the garment shell 22 can be releasably attached to each other at the respective side margins 48, 50 of the panel assemblies. For example, in the illustrated embodiment a fastening component 52 is attached to each side margin 48 of the front panel assembly 26 and is adapted for refastenable engagement with a complementary fastening component 54 attached to each respective side margin 50 of the back panel assembly 28. Although the garment shell 22 as illustrated in FIG. 2 has the side margins 50 of the back panel assembly 28 overlapping the side margins 48 of the front panel assembly 26 upon releasable attachment, the garment shell can instead be configured so that the side margins of the front panel assembly overlap the side margins of the back panel assembly for releasable attachment.

The fastening components 52, 54 can comprise any refastenable fasteners suitable for garments, such as adhesive fasteners, cohesive fasteners, mechanical fasteners, or the like. In particularly suitable embodiments the fastening components 52, 54 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment the fastening components 52 comprise hook fasteners and the fastening components 54 comprise complementary loop fasteners arrayed so that the hook fasteners face generally away from the wearer. Alternatively, the fastening components 52 may comprise loop fasteners and the fastening components 54 may comprise complementary hook fasteners. One skilled in the art will recognize that the shape, density and polymer composition of the hooks and loops may be selected to obtain the desired level of engagement between the fastening components 52, 54. A more aggressive hook material may comprise a material with a greater average hook height and/or a greater percentage of directionally-aligned hooks. It is also contemplated that the fastening components 52, 54 can comprise interlocking similar surface fasteners, or adhesive and cohesive fastening elements such as an adhesive fastener and an adhesive-receptive landing zone or material; or the like.

Loop fastener as used herein refers to a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes, et al., which is incorporated herein by reference.

The loop material may be attached to a base, or backing structure, and the composite then attached to the particular component of the absorbent garment 10, such as the front or back panel assemblies 26, 28 of the garment shell 22, or the loop material may be attached directly to the absorbent garment component so that the component (e.g., the garment shell) serves as a backing for the loop material, or the loop material may be formed integrally with the component (e.g., the garment shell), such as by constructing one or more layers or surfaces of the component to comprise a loop material.

Hook fastener as used herein refers to a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructive releasable attachment. It is understood that the attachment may be of limited lifetime, e.g., gradual degradation of the attachment may occur with repeated engagements and disengagements.

In contrast to the loop fasteners which suitably comprise a flexible fabric, the hook material may advantageously comprise a resilient material to minimize unintentional disengagement of the fastening components 52, 54 as a result of the hook material becoming deformed and catching on clothing or other items. The term "resilient" as used in reference to the hook fasteners refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components 52, 54 as well as other fastening components described later herein are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may be formed integrally with a component of the absorbent garment 10, such as the garment shell 22 in the instance of the fastening components 52, 54, without departing from the scope of this invention.

The fastening components 52, 54 are shown in FIGS. 2 and 3 as having a generally rectangular shape, although they may instead be square, round, oval, curved or other suitable shapes. The fastening components 52, 54 extend along the respective side margins 48, 50 of the front and back panel assemblies 26, 28 generally from the waist ends 56, 58 of the panel assemblies to a position intermediate the waist ends and the leg openings 40 of the garment shell so that the absorbent garment side margins 16, 18 are releasably attached to each other along upper segments of the side seams 19. As an example, the fastening components 52, 54 suitably extend from the front and back waist ends 56, 58 of the garment shell 22 along the side margins 48, 50 thereof in the range of about 25 percent to about 50 percent of the length of the side margins (broadly, about 25 percent to about 50 percent of the length of the side seams 19 of the absorbent garment 10). However, it is understood that the fastening components 52, 54 may be longer or shorter without departing from the scope of this invention. Thus, in the illustrated embodiment, only a portion of the side seams 19 of the absorbent garment are refastenable.

The segment of the garment shell 22 along which the side margins 48, 50 are not releasably attached (e.g., extending from the bottom of the fastening components 52, 54 to the leg openings 40 of the garment shell) are suitably free from any form of attachment. In such an embodiment, the non-refastenable portion of the side seams 19 of the absorbent garment 10 are referred to as being open and the side margins 16, 18 thereof are referred to as being unattached. Alternatively, the side margins 48, 50 of the front and back assemblies 26, 28 of the garment shell 22 may be non-refastenably (e.g., frangibly or permanently) attached to each other along the portion of side margins extending from the bottom of the fastening components to the leg openings 40, such as by adhesive, or by thermal or ultrasonic bonding, or by other suitable attachment techniques.

It is also contemplated that the fastening components 52, 54 may instead extend from the leg openings 40 of the garment shell partially up along the side margins 48, 50 of the front and back panel assemblies 26, 28 (e.g., so that only a lower segment of the side seams 19 of the absorbent garment are refastenable). The side margins 48, 50 extending from the tops of the fastening components 52, 54 to the waist ends 56, 58 of the garment shell 22 may be non-refastenably (e.g., frangibly or permanently) attached to each other in the manner described previously. In other embodiments, the fastening components 52, 54 may extend the entire length of the side margins 48, 50 of the front and back panel assemblies 26, 28 of the garment shell 22 (e.g., such that the side seams 19 of the absorbent garment 10 are refastenable along their full length). Also, while the fastening components 52, 54 are illustrated as being continuous along each respective side margin 48, 50, it is understood that two or more fastening components may be attached to each respective side margin in spaced relationship along the side margin without departing from the scope of this invention.

It is further contemplated that the side margins 48, 50 of the garment shell 22 may instead be permanently or frangibly (e.g., non-refastenably) attached along all or part of the full length thereof whereby no portions of the side margins are refastenable. It is also understood that the garment shell 22 may be formed to omit the side margins 48, 50 thereof, such as by integrally forming the respective front and back panel members 42, 46 on each side of the shell.

The amount of overlap between the side margins 48, 50 of the front and back panel assemblies 26, 28 at the side seams 19 of the garment shell 22 (broadly, the overlap of the side margins 16, 18 of the front and back waist regions 12, 14 of the absorbent garment 10) is suitably in the range of about 0.1 inches (2.5 millimeters (mm)) to about 6 inches (152.4 mm), and more suitably in the range of about 0.5 (12.7 mm) inches to about 3 inches (76.2 mm). It is contemplated that the fastening components 52, 54 on at least one of the front and back panel assemblies 26, 28 may have a width corresponding to the range of overlap to permit a variable fit of the absorbent garment over a relatively wide range of wearer sizes.

The fastening components 52, 54 are suitably attached to the respective front and back panel assemblies 26, 28 by mechanical bonding. As used herein, mechanical bonding refers to non-adhesive bonding, such as by the application of pressure, ultrasonic energy, heat, laser energy or any other suitable form of energy which joins the fastening components to the panel assemblies 26, 28. Alternatively, or additionally, the fastening components 52, 54 may be adhered, such as by adhesive or cohesive means, to the respective front and back panel assemblies 26, 28. It is also contemplated that the fastening components 52, 54 may be formed integrally with the respective front and back panel assemblies 26, 28 and remain within the scope of this invention.

In addition to the front and back panel assemblies 26, 28 of the garment shell 22 being releasably attached to each other at the respective side margins 48, 50 thereof, or as an alternative thereto, it is contemplated that the panel assemblies may be releasably attached to each other at the crotch region 38 of the garment shell to allow the garment shell to be unfastened at the crotch region and pulled up relative to the absorbent assembly 24 for inspecting or otherwise replacing the absorbent assembly. For example, fastening components (not shown in FIGS. 2-4 but indicated at 60, 62 in FIG. 8) may be attached to the front and back panel assemblies 26, 28 of the garment shell 22 generally at the crotch region 38 thereof to permit releasable attachment of the panel assemblies at the crotch region.

To further enhance the appearance of the absorbent garment 10 as well as the fit of the absorbent garment on the wearer's waist, elastic members 64 (e.g., waistband elastics) are operatively joined to the front and back panel assemblies 26, 28 generally at the respective waist ends 56, 58 thereof. For example, as best seen in FIGS. 2 and 3, two elastic members 64 are operatively joined to the front waist end 56 of the garment shell 22 on laterally opposite sides of the absorbent assembly 24. Two more elastic members 64 are operatively joined to the back waist end 58, also on laterally opposite sides of the absorbent assembly 24. The elastic members 64 can be operatively joined to the garment shell 22 while in a stretched condition so that upon retraction the elastic members gather the garment shell at the front and back waist ends 56, 58 to provide a gathered appearance and to further provide an elastic fit of the absorbent garment on the wearer's waist. Alternatively, it is contemplated that a single elastic member (not shown) may be attached to each waist end 56, 58 of the garment shell 22 and extend laterally across all or only a portion of the width of the respective waist end without departing from the scope of this invention.

With further reference to FIGS. 2-6, the absorbent assembly 24 comprises a front waist region 122, a back waist region 124, a crotch region 126 interconnecting the front and back waist regions, an inner surface 128 configured for contiguous relationship with the wearer, and an outer surface 130 opposite the inner surface. The front waist region 122 comprises the portion of the absorbent assembly which, when the absorbent garment 10 is worn, is positioned on the front of the wearer while the back waist region 124 comprises the portion of the absorbent assembly which is positioned on the back of the wearer. The crotch region 126 of the absorbent assembly 24 comprises the portion of the assembly which is positioned between the legs of the wearer and covers the lower torso of the wearer. With additional reference to FIG. 4, the absorbent assembly 24 also has laterally opposite side edges 136 and longitudinally opposite waist ends, respectively designated herein as front waist end 138 and back waist end 140.

The absorbent assembly 24 is suitably "disposable," which as used herein refers to articles that are intended to be discarded after a limited period of use instead of being laundered or otherwise restored for reuse. However, it is contemplated that the absorbent assembly may be re-useable and remain within the scope of this invention. By way of illustration only, various materials and methods for constructing the absorbent assembly 24 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 4:
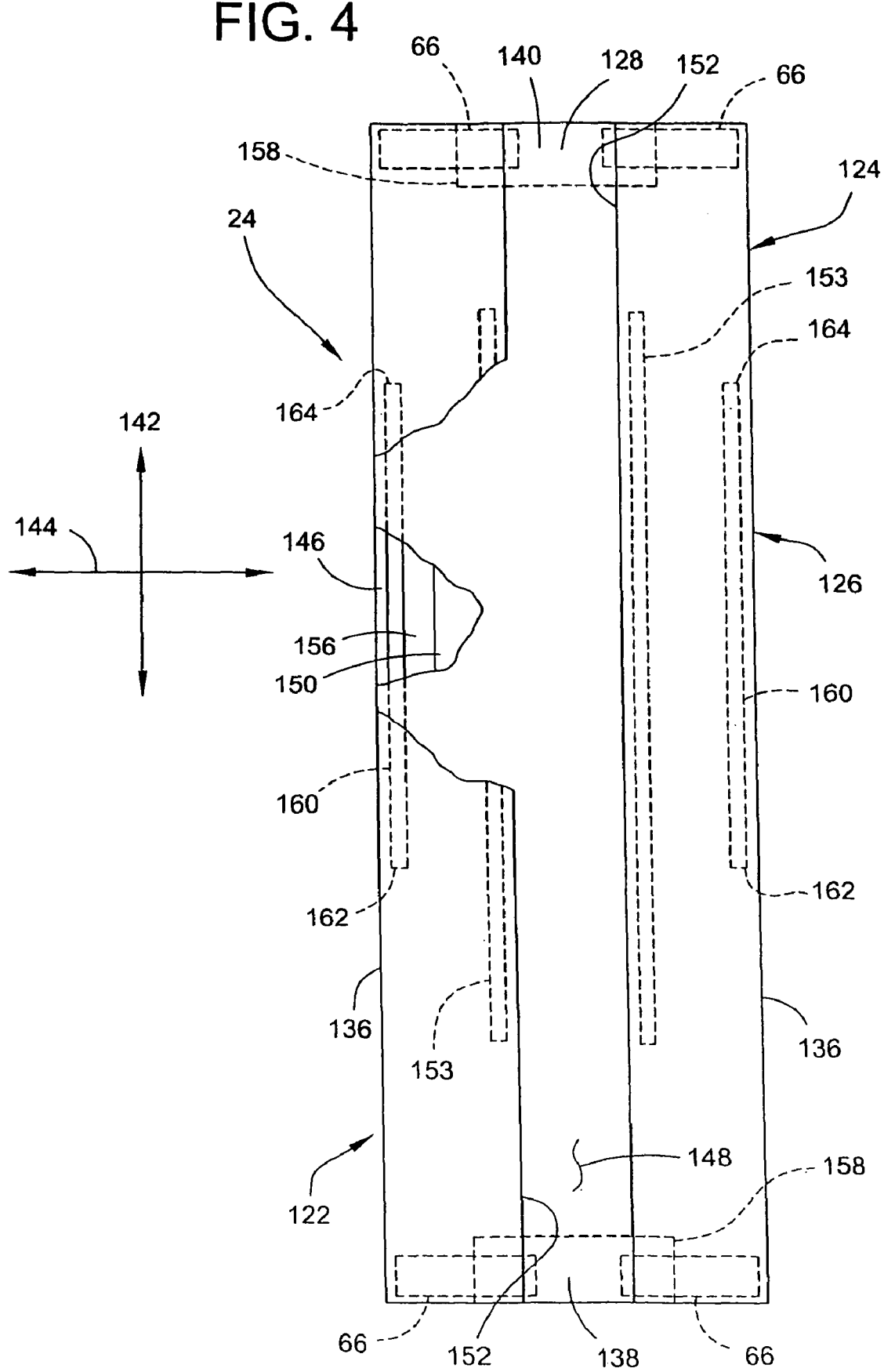
FIG. 4 is a plan view of an absorbent assembly of the absorbent garment of FIG. 1 with the absorbent assembly shown in an unfastened, stretched and laid flat condition, and showing the surface of the absorbent assembly that faces the wearer of the absorbent garment, and with portions cut away to show underlying features.

The absorbent assembly 24 is illustrated in FIGS. 4 and 4a detached from the garment shell 22 and in a laid flat configuration. The absorbent assembly 24 is suitably rectangular in shape and has a longitudinal axis 142 and a transverse, or lateral axis 144. It is understood that the absorbent assembly 24 may be other than rectangular, such as hourglass-shaped, T-shaped, I-shaped or other suitable shape without departing from the scope of this invention. The absorbent assembly 24 comprises an outer cover 146 (FIG. 3), a bodyside liner 148 (FIG. 4) in superposed relationship with the outer cover, an absorbent body 150 disposed between the outer cover and the bodyside liner, and a pair of laterally spaced containment flaps 152 configured to inhibit the transverse flow of body exudates on the liner to the side edges 136 of the absorbent assembly.

The outer cover 146 of the absorbent assembly 24 suitably comprises a material which is substantially liquid impermeable, and may be stretchable or non-stretchable. As used herein, the term "stretchable" refers to a material that may be extensible or elastic. That is, the material may be extended, deformed or the like, without breaking, and may or may not significantly retract after removal of an extending force. As used herein, the term "elastic" refers to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force.

More suitably, the outer cover 146 comprises a multi-layered laminate structure in which at least one of the layers is liquid impermeable. For instance, the outer cover 146 can include a liquid permeable outer layer 154 and a liquid impermeable inner layer 156 (FIG. 4) which are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer 154 can be any suitable material and is desirably one that provides a generally cloth-like texture. One example of such a material is a 20 gsm (grams per square meter) spunbond polypropylene nonwoven web. The outer layer 154 may also be made of those materials described later herein from which the liquid permeable bodyside liner 148 is made.

The inner layer 156 of the outer cover 146 can be both liquid and vapor impermeable, or it may be liquid impermeable and vapor permeable. The inner layer 156 can be manufactured from a thin plastic film, although other flexible liquid impermeable materials may also be used. The liquid impermeable inner layer 156 prevents waste material from wetting articles, such as bed sheets and clothing, as well as the wearer and caregiver. A suitable liquid impermeable film for use as a liquid impermeable inner layer 156 of the outer cover 146 is a 0.02 millimeter polyethylene film commercially available from Pliant Corporation of Schaumburg, Ill., U.S.A.

Alternatively, the outer cover 146 may comprise a single layer of liquid impermeable material. As earlier mentioned, the liquid impermeable material can permit vapors to escape from the interior of the disposable absorbent article, while still preventing liquids from passing through the outer cover 146. For example, the outer cover 146 may be constructed of a microporous polymer film or a nonwoven fabric that has been coated or otherwise treated to impart a desired level of liquid impermeability. One such microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. The single layer outer cover 146 may also be embossed and/or matte finished to provide a more cloth-like appearance.

The liquid permeable bodyside liner 148 is illustrated as overlying the outer cover 146 and absorbent body 150, and may but need not have the same dimensions as the outer cover 146. The bodyside liner 148 is desirably compliant, soft feeling, and non-irritating to the child's skin. Further, the bodyside liner 148 can be less hydrophilic than the absorbent body 150, to present a relatively dry surface to the wearer and to permit liquid to readily penetrate through the liner. Alternatively, the bodyside liner 148 can be more hydrophilic or can have essentially the same affinity for moisture as the absorbent body 150 to present a relatively wet surface to the wearer to increase the sensation of being wet. This wet sensation can be useful as a training aid. The hydrophilic/hydrophobic properties can be varied across the length, width and depth of the bodyside liner 148 and absorbent body 150 to achieve the desired wetness sensation or leakage performance.

The bodyside liner 148 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 148. For example, the bodyside liner 148 can be composed of a meltblown or spunbonded web of polyolefin fibers. The bodyside liner can also be a bonded-carded web composed of natural and/or synthetic fibers. The bodyside liner 148 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220 UP from Henkel Corporation of Ambler, Pa. in an active ratio of 3:1. The surfactant can be applied by any conventional means, such as spraying, printing, brush coating or the like. The surfactant can be applied to the entire bodyside liner 148 or can be selectively applied to particular sections of the bodyside liner, such as the medial section along the longitudinal center line.

One example of a suitable liquid permeable bodyside liner 148 is a nonwoven bicomponent web having a basis weight of about 27 gsm. The nonwoven bicomponent web can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent body 150 (FIG. 4) is positioned between the outer cover 146 and the bodyside liner 148, which can be joined together by any suitable means such as adhesives, ultrasonic bonds, thermal bonds, or the like. The absorbent body 150 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 150 can suitably comprise a matrix of hydrophilic fibers, such as a web of cellulosic fluff, mixed with particles of a high-absorbency material commonly known as superabsorbent material. In a particular embodiment, the absorbent body 150 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent body 150 to better contain and absorb body exudates. The concentration of the superabsorbent particles can also vary through the thickness of the absorbent body 150. Alternatively, the absorbent body 150 can comprise a laminate of fibrous webs and superabsorbent material, a foam or other suitable web construction.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 10 times its weight in water, and suitably is capable of absorbing more than about 25 times its weight in water.

In one embodiment, the absorbent body 150 comprises a blend of wood pulp fluff and superabsorbent material. One suitable type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. In general, the superabsorbent material is present in the absorbent body 150 in an amount of from 0 to about 90 weight percent based on total weight of the absorbent assembly. The absorbent body 150 may or may not be wrapped or encompassed by a suitable tissue wrap that aids in maintaining the integrity and/or shape of the absorbent assembly during use.

The containment flaps 152 are located generally adjacent to the side edges 136 of the absorbent assembly 24, and can extend longitudinally along the entire length of the absorbent assembly 24 as shown in FIG. 4 or only partially along the length of the absorbent assembly. Flap elastic members 153 (FIG. 4) are operatively joined with the containment flaps 152 in a suitable manner as is well known in the art, such as by adhering the elastic members to the flaps while the elastic members are in a stretched condition so that the flaps are biased by the elastic members to a longitudinally gathered configuration. The elasticized containment flaps 152 also define a partially unattached distal edge (e.g., unattached to the liner 148) which assumes an upright configuration in at least the crotch region 126 of the absorbent assembly 24 during wear to form a seal (e.g., an elastic fit) against the wearer's body. Suitable constructions and arrangements for the containment flaps 152 are generally well known to those skilled in the art and are described in U.S. Pat. No. 4,704,116 issued Nov. 3, 1987 to Enloe, which is incorporated herein by reference. It is understood, however, that the containment flaps 152 may be omitted without departing from the scope of this invention.

To further enhance the fit of the absorbent garment 10 on the wearer and to further inhibit leakage of body exudates, the absorbent assembly can also have waist elastic members 158 (FIGS. 2 and 4) and leg elastic members 160 (FIG. 4), as are known to those skilled in the art. The waist elastic members 158 can be operatively joined to the absorbent assembly 24 at the waist ends 138 and 140, such as by attaching the elastic members to the outer cover 146 and/or the bodyside liner 148 while the elastic members are in a stretched condition, so that upon retraction the elastic members gather the absorbent assembly at the waist ends to provide an elastic fit against the wearer's waist. In the illustrated embodiment the elastic members 158 which are operatively joined to the absorbent assembly 24, and the elastic members 64 which are operatively joined to the garment shell 22 on laterally opposite sides of the absorbent assembly, together provide an elastic fit of the absorbent garment 10 against substantially the entire waist of the wearer. The elastic members 158 are shown in FIG. 4 as extending only partially across the respective front and back waist ends 138, 140 of the absorbent assembly 24. It is understood, however, that the elastic members 158 may extend laterally across the full width of the absorbent assembly 24 at one or both waist ends 138, 140 without departing from the scope of this invention.

The leg elastic members 160 can be operatively joined to the outer cover 146 and/or the bodyside liner 148 and extend longitudinally adjacent the opposite side edges 136 generally through the crotch region 126 of the absorbent assembly 24. Each leg elastic member 160 has a front terminal point 162 and a back terminal point 164, which represent the longitudinal ends of the elastic gathering caused by the leg elastic members.

The flap elastic members 153, the waist elastic members 158 (as well as the elastic members 64 operatively joined with the garment shell 22), and the leg elastic members 160 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

The absorbent assembly 24 can also incorporate other materials or components designed primarily to receive, temporarily store, and/or transport liquid along the mutually facing surface with the absorbent body 150, thereby maximizing the absorbent capacity of the absorbent assembly. For example, one suitable additional component is commonly referred to as a surge layer (not shown). Surge layers are generally well known in the art as being constructed to quickly collect and temporarily hold liquid surges, and to transport the temporarily held liquid to the absorbent body 150.

Various woven and non-woven fabrics can be used to construct the surge layer. For example, the surge layer may be a layer made of a meltblown or spunbond web of synthetic fibers, such as polyolefin fibers. The surge layer may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge layer may be composed of a substantially hydrophobic material, and the hydrophobic material may optionally be treated with a surfactant or otherwise processed to impart a desired level of wettability and hydrophilicity.

Examples of materials suitable for the surge layer are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference in a manner consistent with the present document.

With particular reference to FIGS. 2-4a, the absorbent assembly 24 is releasably attached to the garment shell 22 to permit detachment and replacement of the absorbent assembly (or detachment and laundering thereof where the absorbent assembly is not disposable) without having to dispose of, launder or otherwise replace the garment shell 22 with a new garment shell. More suitably, the front and back waist ends 138, 140 of the absorbent assembly 24 are releasably attached to the garment shell 22 generally at the front and back waist ends 56, 58 thereof, respectively. For example, fastening components 66 are attached to the outer cover 146 of the absorbent assembly 24 generally at the front waist end 138 thereof in laterally spaced relationship with each other. Corresponding laterally spaced complimentary fastening components 68 are attached to the inner surface of the garment shell 22 at the front waist end 56 thereof for releasable attachment to the fastening components 66 at the front waist end 138 of the absorbent assembly 24. Additional fastening components 66 can be attached to the outer cover 146 of the absorbent assembly 24 generally at the back waist end 140 thereof with corresponding fastening components 68 being attached to the inner surface of the back waist end 58 of the garment shell 22 for releasable attachment to the fastening components 66 at the back waist end of the absorbent assembly.

The fastening components 66, 68 can comprise any refastenable fasteners suitable for garments as described previously herein, such as adhesive fasteners, cohesive fasteners, mechanical fasteners, or the like. In particularly suitable embodiments the fastening components 66, 68 comprise mechanical fastening elements provided by interlocking geometric shaped materials such as hooks, loops, bulbs, mushrooms, arrowheads, balls on stems, male and female mating components, buckles, snaps, or the like. For example, in the illustrated embodiment the fastening components 66 attached to the front and back waist ends 138, 140 of the absorbent assembly 24 comprise hook fasteners and the fastening components 68 attached to the front and back waist ends 56, 58 of the garment shell 22 comprise complementary loop fasteners.

Alternatively, the fastening components 66 may comprise loop fasteners and the fastening components 68 may comprise complementary hook fasteners. In another embodiment, the fastening components 66, 68 can comprise interlocking similar surface fasteners, or adhesive and cohesive fastening elements such as an adhesive fastener and an adhesive-receptive landing zone or material, or the like. One skilled in the art will recognize that the shape, density and polymer composition of the hooks and loops may be selected to obtain the desired level of engagement between the fastening components 66, 68. A more aggressive hook material may comprise a material with a greater average hook height and/or a greater percentage of directionally-aligned hooks.

The fastening components 66, 68 are illustrated as being rectangular in shape, although it is understood that the fastening components may be square, circular, curved or other suitable shape. The fastening components 66, 68 suitably each have a width (e.g., determined parallel to the longitudinal axis of the garment 10 in the illustrated embodiment) in the range of about 3 mm to about 50 mm, and a length (e.g., determined parallel to the transverse axis of the garment 10 in the illustrated embodiment) in the range of about 20 mm to about 175 mm. However, it is contemplated that the fastening components 66, 68 may be larger or smaller in width and/or length without departing from the scope of this invention. It is also contemplated that single fastening components 66 may be attached to the absorbent assembly 24 at the respective front and back waist ends 138, 140. In such an embodiment, the single fastening components 66 may suitably be laterally positioned centrally on the absorbent assembly 24 at the respective waist ends 138, 140 thereof and may extend partially or fully across the full width of the absorbent assembly at the waist ends.

The fastening components 66 of the illustrated embodiment may be attached to the front and back waist ends 138, 140 of the absorbent assembly 24 by adhesive, by thermal bonding or ultrasonic bonding, or by any other suitable attachment technique. The fastening components 68 may be attached to the front and back waist ends 56, 58 of the garment shell 22 by any of these attachment techniques as well, and may be attached using the same attachment technique used to attach the fastening components 66 to the front and back waist ends 138, 140 of the absorbent assembly 24, or by a different attachment technique. It is also contemplated that the fastening components 66 may be attached to the front and back waist ends 138, 140 of the absorbent assembly 24 by being formed integrally therewith. Likewise, the fastening components 68 may be formed integrally with the respective front and back waist ends 56, 58 of the garment shell 22.

With the absorbent assembly 24 releasably attached to the garment shell 22, the elasticized side edges 136 of the absorbent assembly generally define laterally opposite elastic leg openings 170 of the absorbent assembly (broadly, inner leg openings of the absorbent garment 10) whereat the absorbent assembly provides an elastic fit against at least part of the wearer's legs. The waist ends 138, 140 of the absorbent assembly 24 together with the waist ends 56, 58 of the garment shell 22 together broadly define the waist opening 20 of the absorbent garment 10. The leg openings 40 of the garment shell 22 broadly define outer leg openings of the absorbent garment 10, separate (e.g., discrete) from the absorbent assembly leg openings 170, whereat the absorbent garment hangs generally loose about the wearer's legs.

While not shown in the drawings, it is contemplated that the absorbent assembly 24 may additionally be releasably attached to the garment shell 22 other than at the waist ends 138, 140 of the absorbent assembly and remain within the scope of this invention. For example, the absorbent assembly 24 may be secured to the garment shell longitudinally intermediate the waist ends 138, 140 of the absorbent assembly, e.g., and more suitably within the crotch region 126 of the absorbent assembly.

Figure 5:
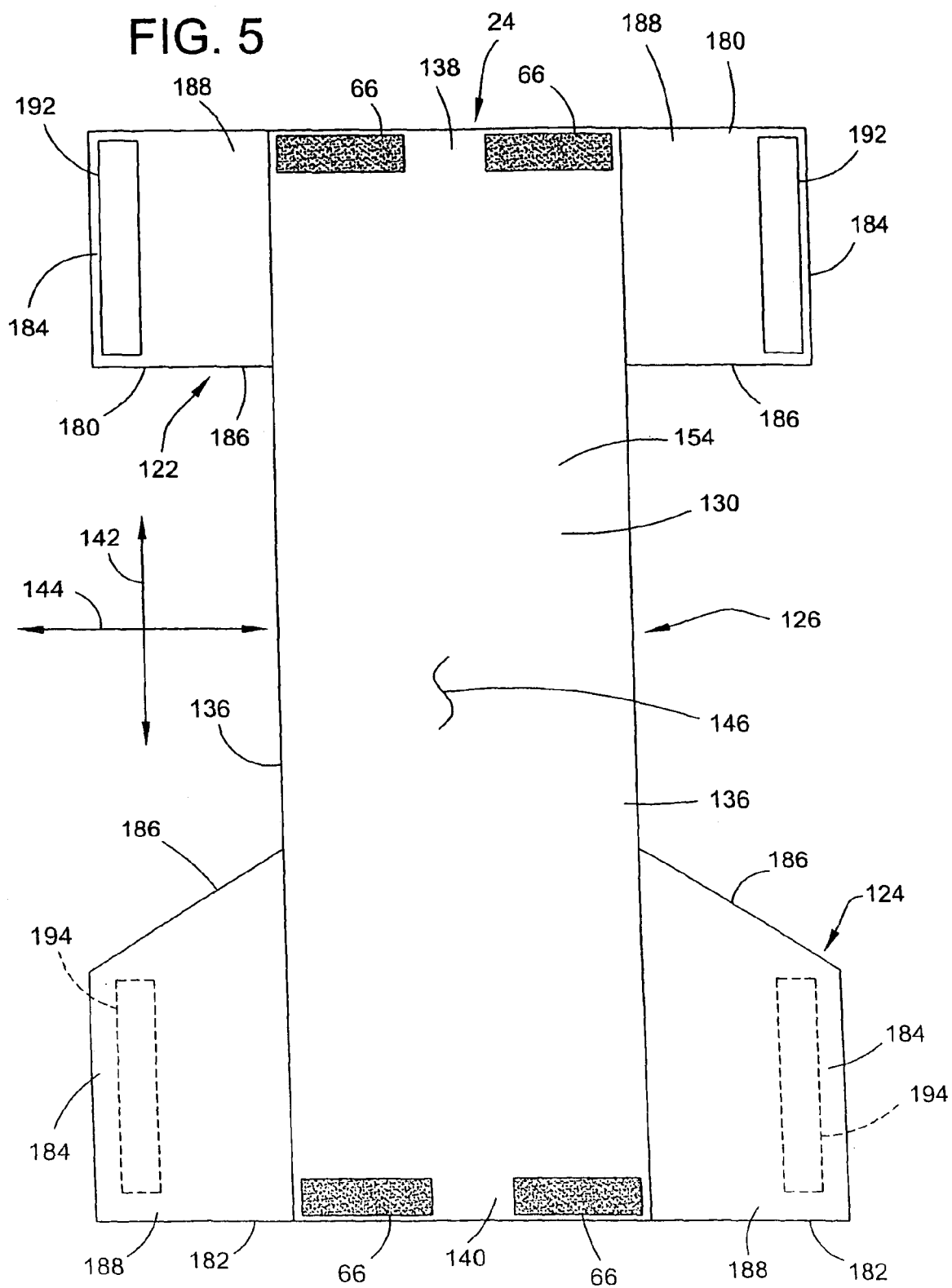
FIG. 5 is a plan view similar to FIG. 4a illustrating an alternative embodiment of an absorbent assembly.

In an alternative embodiment of the absorbent assembly 24 as shown in FIG. 5 (as well as in a second embodiment of an absorbent garment 10 shown in FIG. 6 and described further below), the absorbent assembly 24 may be a brief-style absorbent assembly such as children's training pants, swim pants or adult incontinence products which are configured for wearing about the full waist of the wearer. That is, the absorbent assembly 24 could be worn on the wearer's waist without being attached to the garment shell 22. More particularly, in addition to the components illustrated in FIG. 4 and described previously herein, the absorbent assembly 24 illustrated in FIGS. 5 and 6 further comprises front and back side panels, designated 180 and 182, respectively, disposed generally on each side of the absorbent assembly 24 at the respective front and back waist regions 122, 124 of the absorbent assembly and extending transversely outward therefrom. The side panels 180, 182 may be attached to the bodyside liner 148 and/or to the outer cover 146 of the absorbent assembly 24 by adhesive, or by thermal or ultrasonic bonding, or by other suitable attachment techniques known to those skilled in the art. Alternatively, the side panels 180, 182 can be formed as an integral portion of a component of the absorbent assembly 24. For example, the side panels 180, 182 can comprise a generally wider portion of the outer cover 146, the bodyside liner 148, and/or another component of the absorbent assembly 24.

The front and back side panels 180, 182 have respective outer edges 184 which broadly define the side edges of the absorbent assembly 24 at the front and back waist regions 122, 124 thereof. The side panels 180, 182 also have respective leg end edges 186 disposed toward the longitudinal center of the absorbent assembly 24, and respective waist end edges 188 which further define the respective front or back waist end 138, 140 of the absorbent assembly 24. The leg end edges 186 of the back side panels 182 are illustrated as being curved and/or angled relative to the transverse axis 144 to provide a better fit of the absorbent assembly 24 about the wearer's legs. However, it is understood that the leg end edges 186 of the front side panels 180 may additionally, or alternatively, be curved or angled, or none of the leg end edges may be curved or angled, without departing from the scope of this invention.

The side panels 180, 182 suitably comprise a stretchable material, and more suitably an elastic material, capable of stretching in a direction generally parallel to the transverse axis 144 of the absorbent assembly 24. Suitable elastic materials, as well as one process of incorporating elastic side panels into brief-style absorbent assemblies, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or nonwoven materials, such as those described above as being suitable for the outer cover 146 or bodyside liner 148; mechanically pre-strained composites; stretchable but inelastic (e.g., extensible) materials; or non-stretchable materials.

Figure 6:
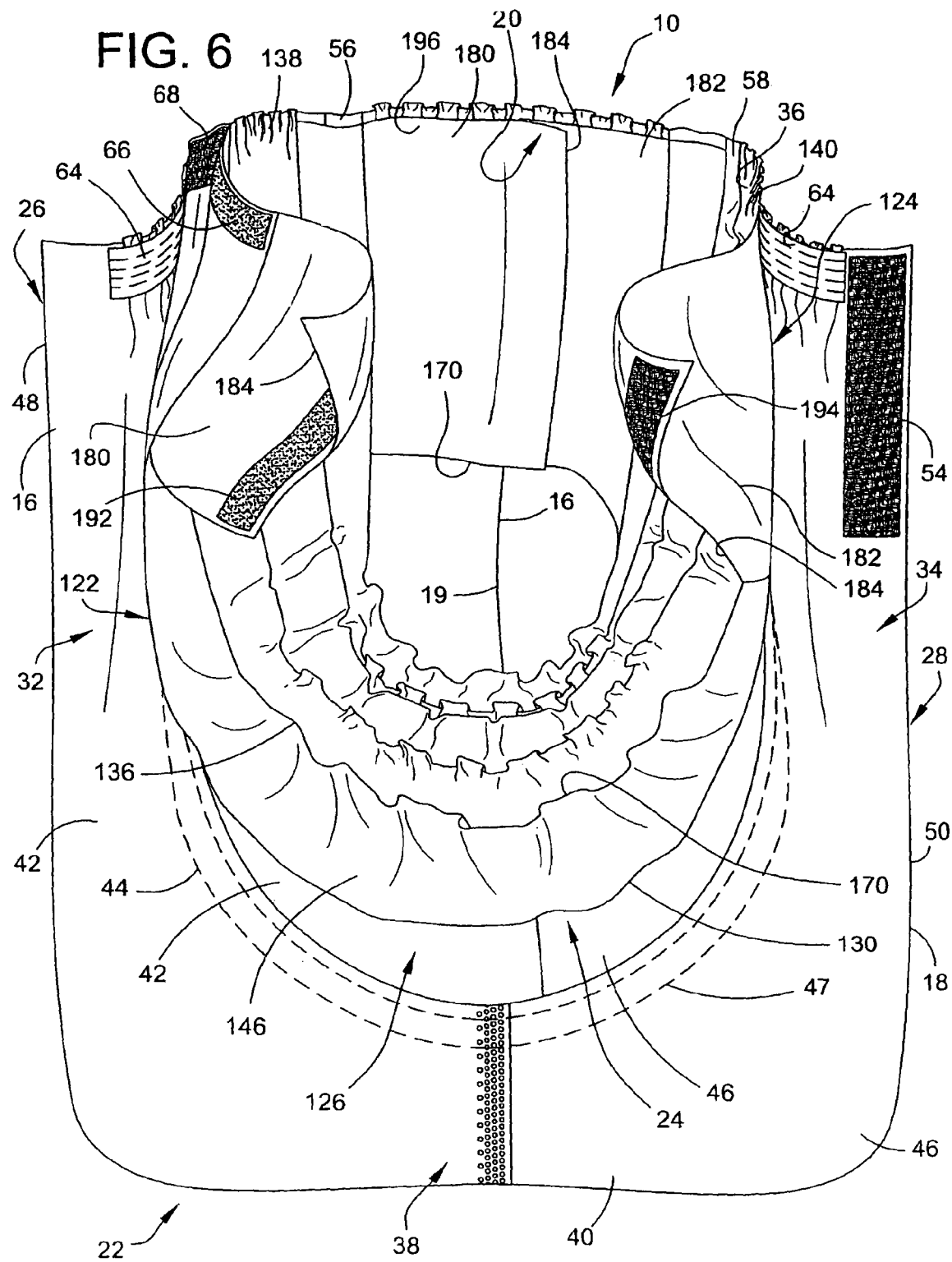
FIG. 6 is a side elevation of a second embodiment of an absorbent garment incorporating the absorbent assembly of FIG. 5, with a side seam of the absorbent garment shown in an unfastened condition and one pair of side panels of the absorbent assembly also shown in an unfastened condition.

Still referring to FIGS. 5 and 6, the absorbent assembly 24 of this embodiment further comprises laterally spaced first fastening components 192 attached to the front side panels 180 generally at the outer edges 184 thereof and complementary second fastening components 194 attached to the back side panels 182 generally at the outer edges thereof and adapted for refastenable engagement with the first fastening components to releasably attach the side panels together to thereby define a three-dimensional configuration of the absorbent assembly that can be worn about the waist of the wearer. The fastening components 192, 194 can comprise any of the refastenable fasteners previously described herein as being suitable for absorbent garments, such as adhesive fasteners, cohesive fasteners, mechanical fasteners, or the like. In particular embodiments the fastening components 192, 194 comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 192 comprise hook fasteners and the second fastening components 194 comprise complementary loop fasteners. Alternatively, the first fastening components 192 may comprise loop fasteners and the second fastening components 194 may comprise complementary hook fasteners. In another embodiment, the fastening components 192, 194 can comprise interlocking similar surface fasteners, or adhesive and cohesive fastening elements such as an adhesive fastener and an adhesive-receptive landing zone or material; or the like. It is also contemplated that the side panels 180, 182 of the absorbent assembly may instead be non-refastenably (e.g., permanently or frangibly) attached together, such as by adhesive, by thermal bonding or ultrasonic bonding, or by other suitable attachment techniques and remain within the scope of this invention.

In the illustrated embodiment, the back side panels 182 overlap the front side panels 180 upon releasable attachment of the side panels. However, it is understood that the front side panels 180 may instead overlap the back side panels 182 without departing from the scope of this invention. The side panels 180, 182 are otherwise unattached to the garment shell 22 so that upon assembling the absorbent garment 10, the side panels are attached to each other and then the side margins 48, 50 of the front and back panel assemblies 26, 28 of the garment shell 22 are separately attached to each other.

As shown in FIG. 6, with the side panels 180, 182 attached to each other to define the three-dimensional configuration of the absorbent assembly 24, the front and back waist ends 138, 140 of the absorbent assembly together define a waist opening 196 of the absorbent assembly separate from the waist opening 36 of the garment shell 22. In such an embodiment, the waist opening 196 of the absorbent assembly 24 broadly defines the waist opening 20 of the absorbent garment 10. The side edges 136 of the absorbent assembly 24, including the leg end edges 186 of the side panels 180, 182, define the elastic leg openings 170 (broadly, the inner leg openings of the absorbent garment 10) of the absorbent assembly 24 about which the absorbent assembly provides an elastic fit against the wearer's leg. The attached side margins 48, 50 of the front and back panel assemblies 26, 28 of the garment shell 22 broadly define the side margins 16, 18 of the absorbent garment 10 which are releasably attached along all or part of the side seams 19 of the absorbent garment. As in the embodiment of FIG. 3, the leg openings 40 of the garment shell 22 shown in FIG. 6 broadly define outer leg openings of the absorbent garment 10 separate (e.g., discrete) from the leg openings 170 of the absorbent assembly whereat the absorbent garment hangs generally loose about the wearer's legs.

Figure 7:
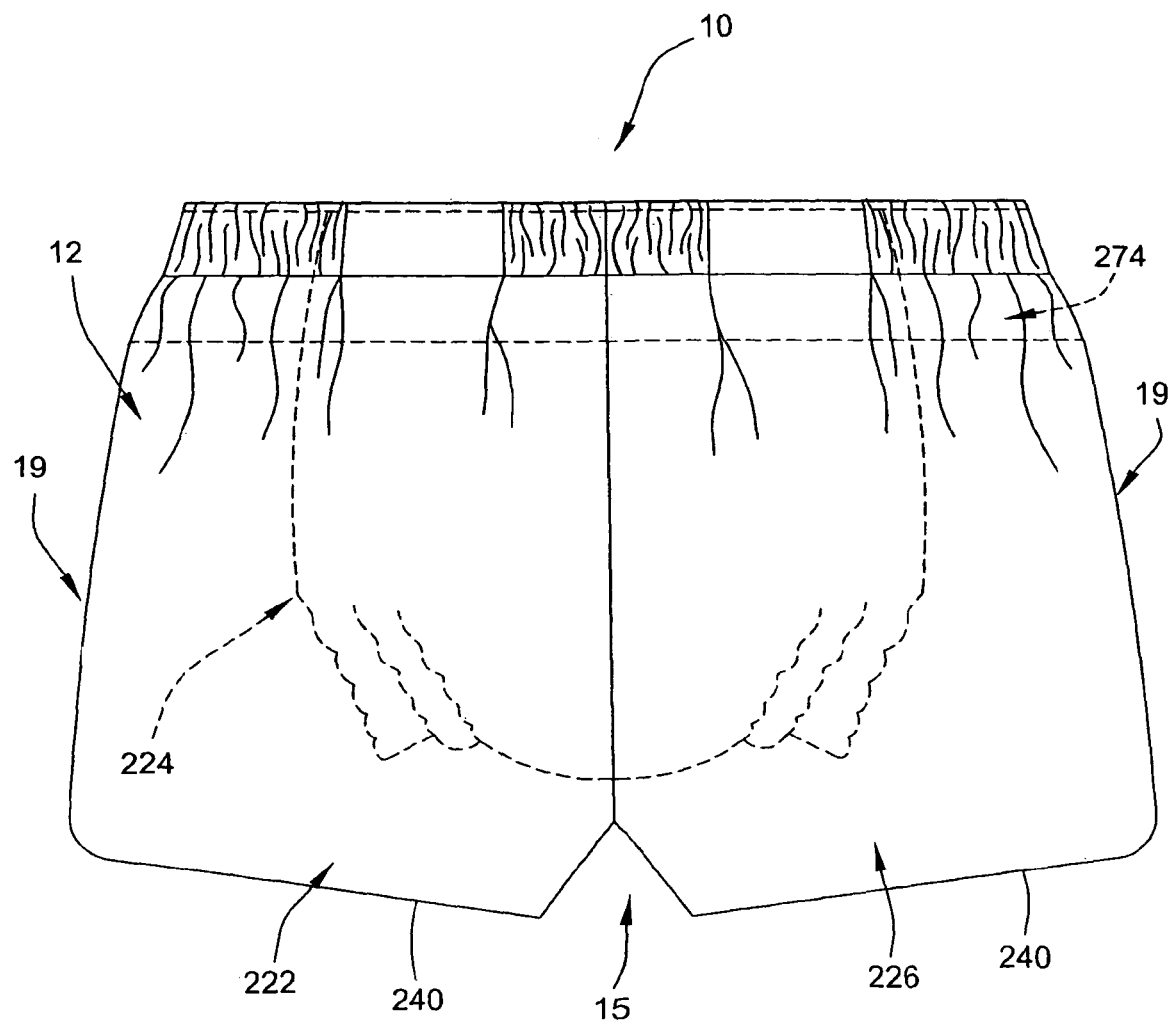
FIG. 7 is a front elevation of a third embodiment of an absorbent garment of the present invention.
Figure 8:
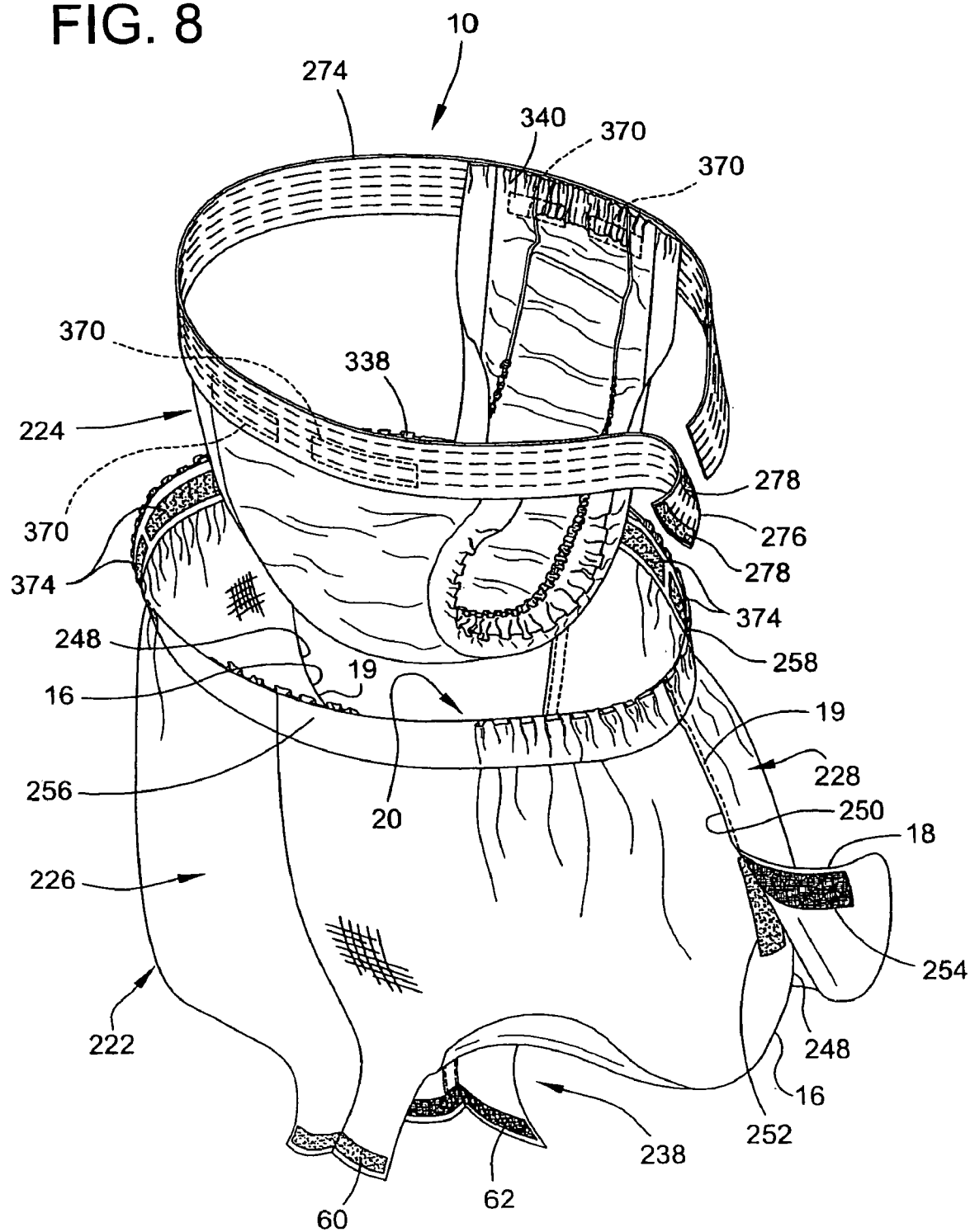
FIG. 8 is an exploded perspective of the absorbent garment of FIG. 7.
Figure 9:
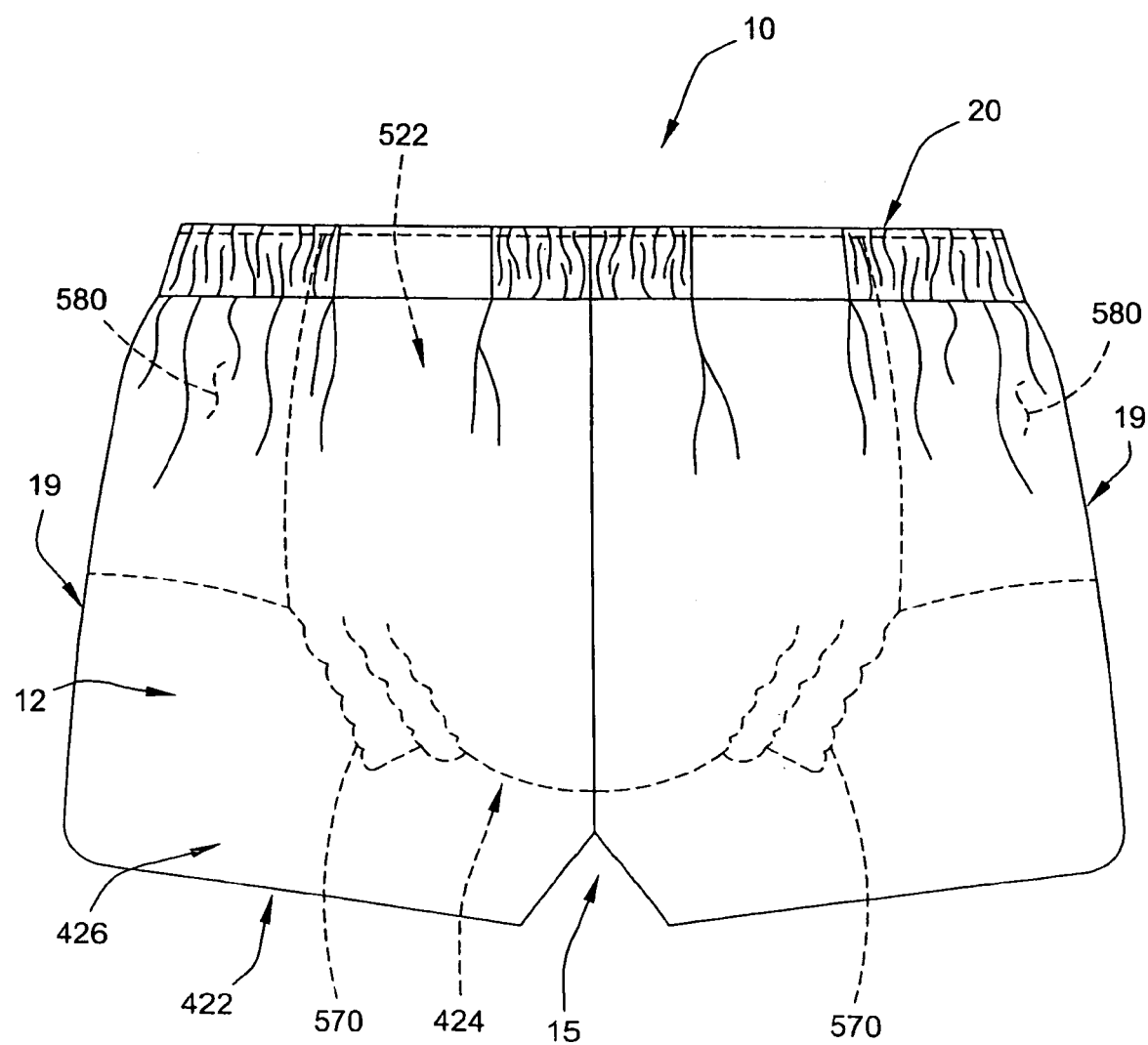
FIG. 9 is a front elevation of a fourth embodiment of an absorbent garment of the present invention.
Figure 10:
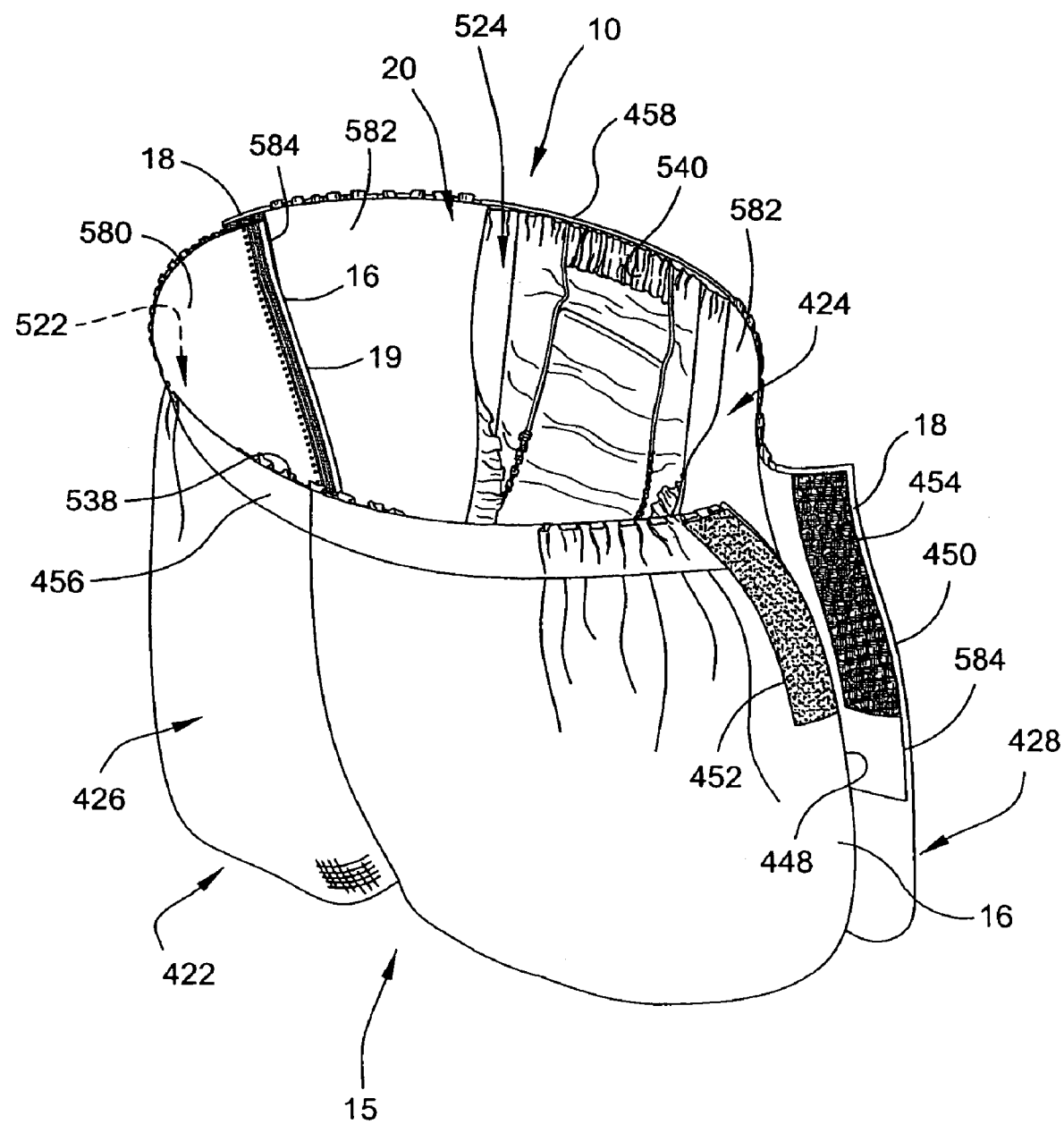
FIG. 10 is a perspective of a fifth embodiment of an absorbent garment of the present invention, with a side seam of the absorbent garment shown in an unfastened condition.
Figure 11:
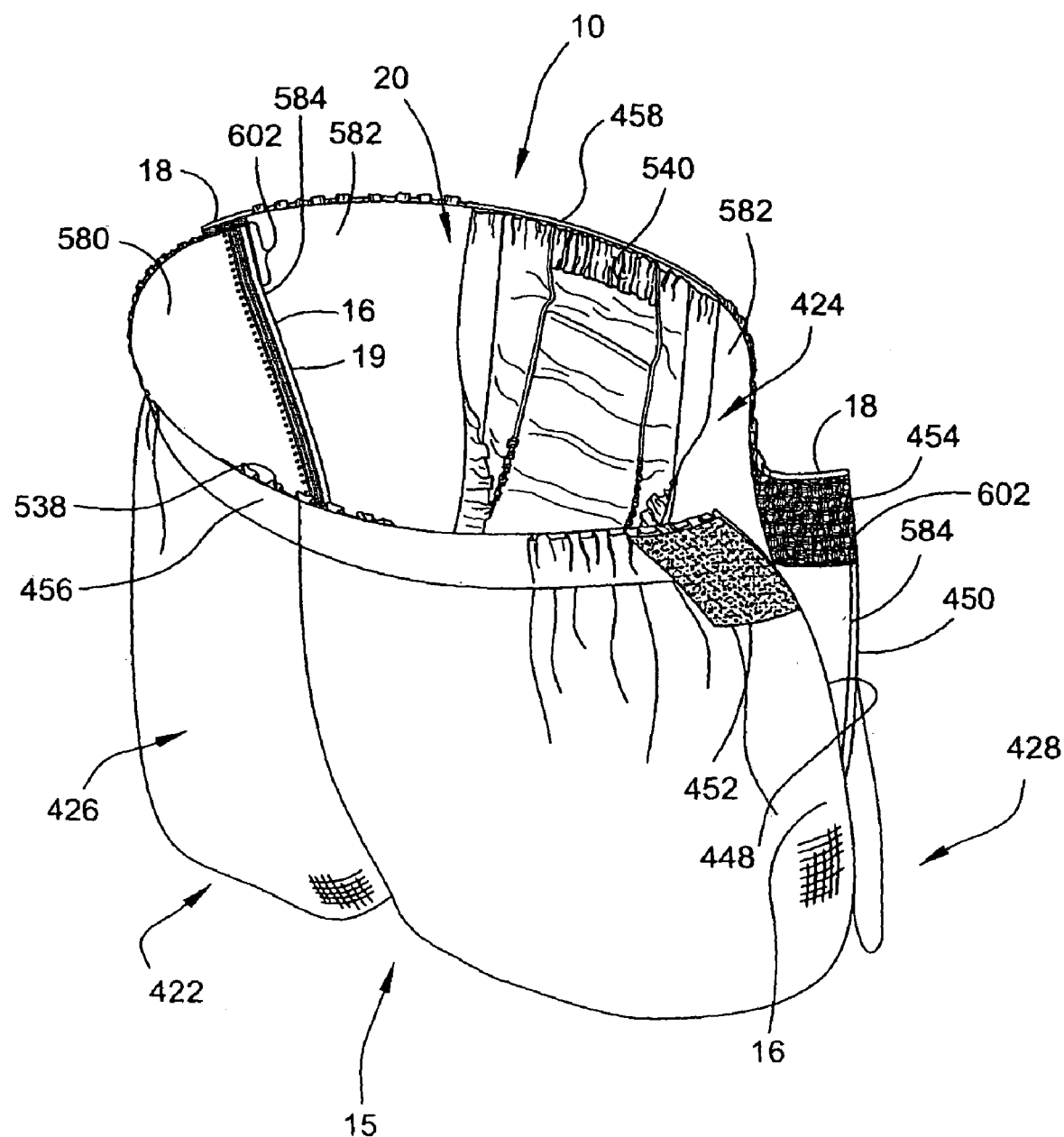
FIG. 11 is a perspective of a sixth embodiment of an absorbent garment of the present invention, with a side seam of the absorbent garment shown in an unfastened condition.

Referring now to FIGS. 7 and 8, an absorbent garment 10 according to another embodiment of the present invention comprises a garment shell, generally indicated at 222, an absorbent assembly, generally indicated at 224 disposed within the garment shell, and a waist belt, generally indicated at 274 and configured for extending about the waist of the wearer to provide a suitable fit of the absorbent garment on the wearer's waist. The waist belt 274 is suitably stretchable, and more suitably elastic. For example, the waist belt 274 is suitably stretchable to a length in the range of about 120 percent to about 200 percent of its unstretched length.

The waist belt 274 is suitably constructed of elastomeric materials including, but not limited to elastic strands, elastic films, nonwoven elastic webs, meltblown or spunbond elastomeric fibrous webs. Examples of suitable elastomeric materials include ESTANE® elastomeric polyurethanes (available from B.F. Goodrich and Company located in Cleveland, Ohio), PEBAX® elastomers (available from AtoChem located in Philadelphia, Pa.), HYTREL® elastomeric polyester (available from E.I. DuPont de Nemours located in Wilmington Del.), KRATON® elastomer (available from Kraton, Inc. of Houston, Tex.), strands of LYCRA® elastomer (available from E.I. DuPont de Nemours located in Wilmington Del.) or the like, as well as combinations thereof. Suitable elastomeric materials may be braided, knit, woven or otherwise combined with natural fibers, or synthetic fibers such as polyester, nylon or polyolefins.

Alternatively, the waist belt 274 may be constructed of an extensible material, or it may be constructed of a non-stretchable material, without departing from the scope of this invention. The waist belt 274 suitably has a width of at least about 6 mm, and more suitably in the range of about 20 mm to about 80 mm. As an example, the waist belt 274 shown in FIGS. 7 and 8 has a width of approximately 38 mm.

In the illustrated embodiment, the waist belt 274 is suitably sized in length so as to define an overlapping end portion 276 upon extending about the wearer's waist whereby the end portion overlaps an underlying portion (e.g., the portion extending about the wearer's waist) of the belt. Fastening components 278 can be attached to the overlapping end portion 276 of the waist belt 274 for use in releasably attaching the overlapping end portion of the belt to the underlying portion to secure the belt on the wearer's waist. For example, the waist belt 274 shown in FIG. 8 has a pair of fastening components 278, such as hook fasteners, spaced lengthwise from each other generally at the overlapping end portion 276 of the belt. The hook fasteners may be attached to the waist belt 274 by adhesive, or by thermal or ultrasonic bonding, or by other suitable attachment techniques.

The waist belt 274 material can also comprise a suitable loop material for releasable attachment of the hook fasteners thereto. It is understood that more than two fastening components 278 may be attached to the overlapping end portion 276 of the waist belt 274, or that a single fastening component may be secured to the waist belt and may extend longitudinally along all or part of the overlapping end portion of the waist belt. It is also understood that instead of the waist belt 274 material providing a suitable loop material, one or more complementary fastening components (not shown) may be attached to the underlying portion of the waist belt and adapted for releasable attachment to the fastening components 278 on the overlapping end portion 276 of the waist belt. In such an embodiment, the fastening components attached to the waist belt 274 may comprise any of the fastening components described previously herein as being suitable for absorbent garments. It is further contemplated that the overlapping end portion 276 of the waist belt 274 may be permanently attached to the underlying portion of the belt without departing from the scope of this invention.

The garment shell 222 is substantially similar to the garment shell 22 of FIGS. 1-3 in that it comprises front and back panel assemblies, generally indicated at 226 and 228, respectively, attached to each other at respective side margins 248, 250 to form the three-dimensional configuration of the garment shell. In the embodiment illustrated in FIGS. 7 and 8, the side margins 248, 250 of the front and back panel assemblies 226, 228 are permanently attached to each other generally from front and back waist ends 256, 258 of the garment shell 222 down to a position intermediate the waist ends and leg openings 240 of the garment shell (e.g., about half way between the waist ends and the leg openings in the illustrated embodiment). The side margins 248, 250 of the front and back panel assemblies 226, 228 are otherwise suitably releasably attached to each other, e.g., from the bottom of the permanent attachment down to the leg openings 240 of the garment shell 222, by suitable fastening components 252, 254 which are similar in construction to the fastening components 52, 54 of FIG. 2. Thus, it is understood that the side seams 19 of the absorbent garment 10 of this embodiment are releasably attached along only a lower portion of the side seams.

Alternatively, the front and back panel assemblies 226, 228 of the garment shell 222 may be attached in substantially the same manner as those shown in FIG. 2 and described previously herein. It is understood that the front and back panel assemblies 226, 228 may instead be permanently attached to each other along the full length of the side margins 248, 250, or they may be releasably attached to each other along the full length of the side margins. It is also contemplated that the front and back panel assemblies 226, 228 of the garment shell 222 may be permanently or releasably attached to each other along only a portion of the length of the side margins 248, 250 and be otherwise free from attachment along the remaining portion or portions of the side margins without departing from the scope of this invention. In the illustrated embodiment, the front and back panel assemblies 226, 228 are further releasably attached to each other at a crotch region 238 of the garment shell 222 by suitable fastening components 60, 62. However, it is understood that the front and back panel assemblies 226, 228 of the garment shell 222 may be permanently attached to each other at the crotch region 238, or that the crotch region of the garment shell may be omitted altogether (such as where the garment shell is intended to resemble a skirt).

Figure 12:
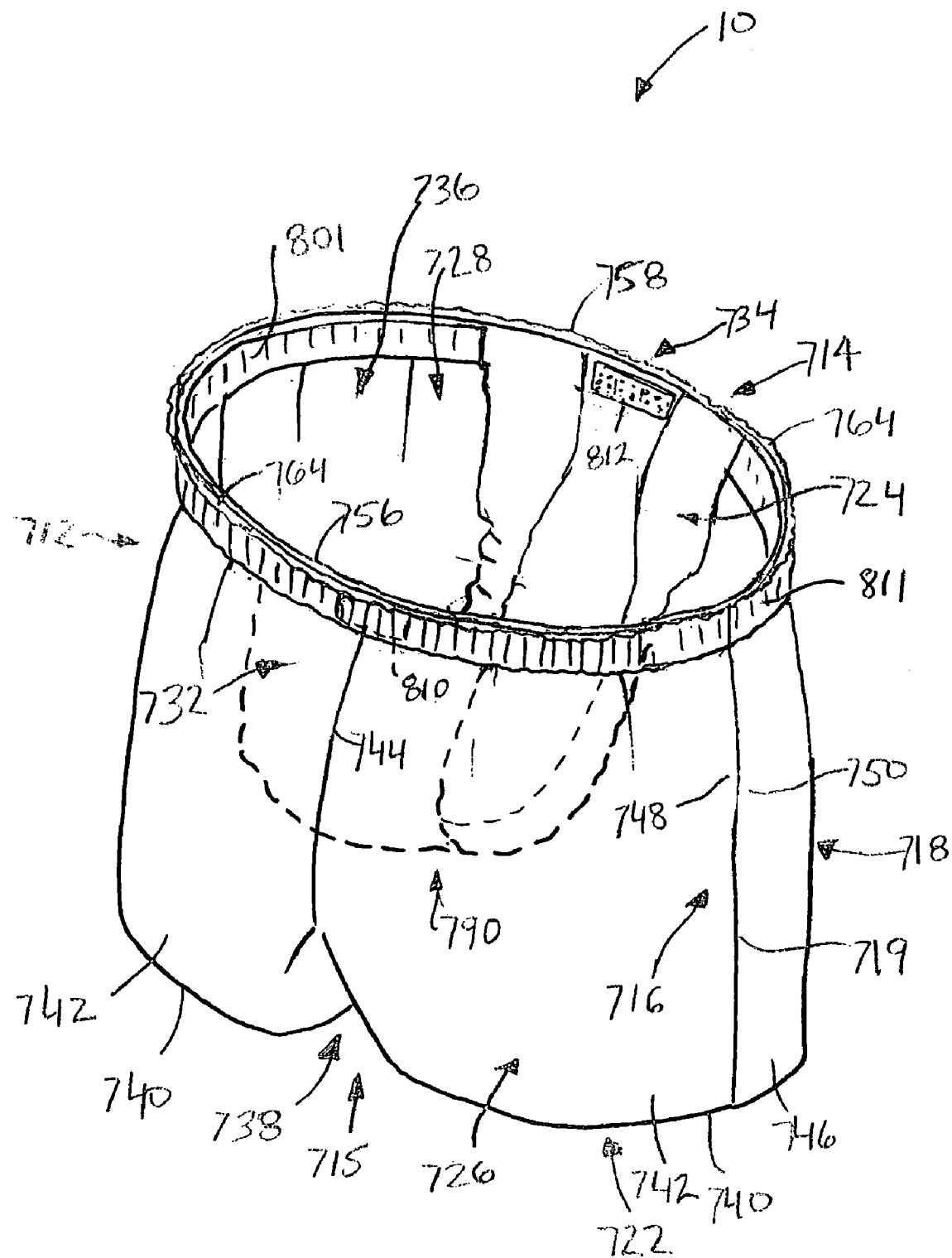
FIG. 12 is perspective of a seventh embodiment of an absorbent garment of the present invention.
Figure 12A:
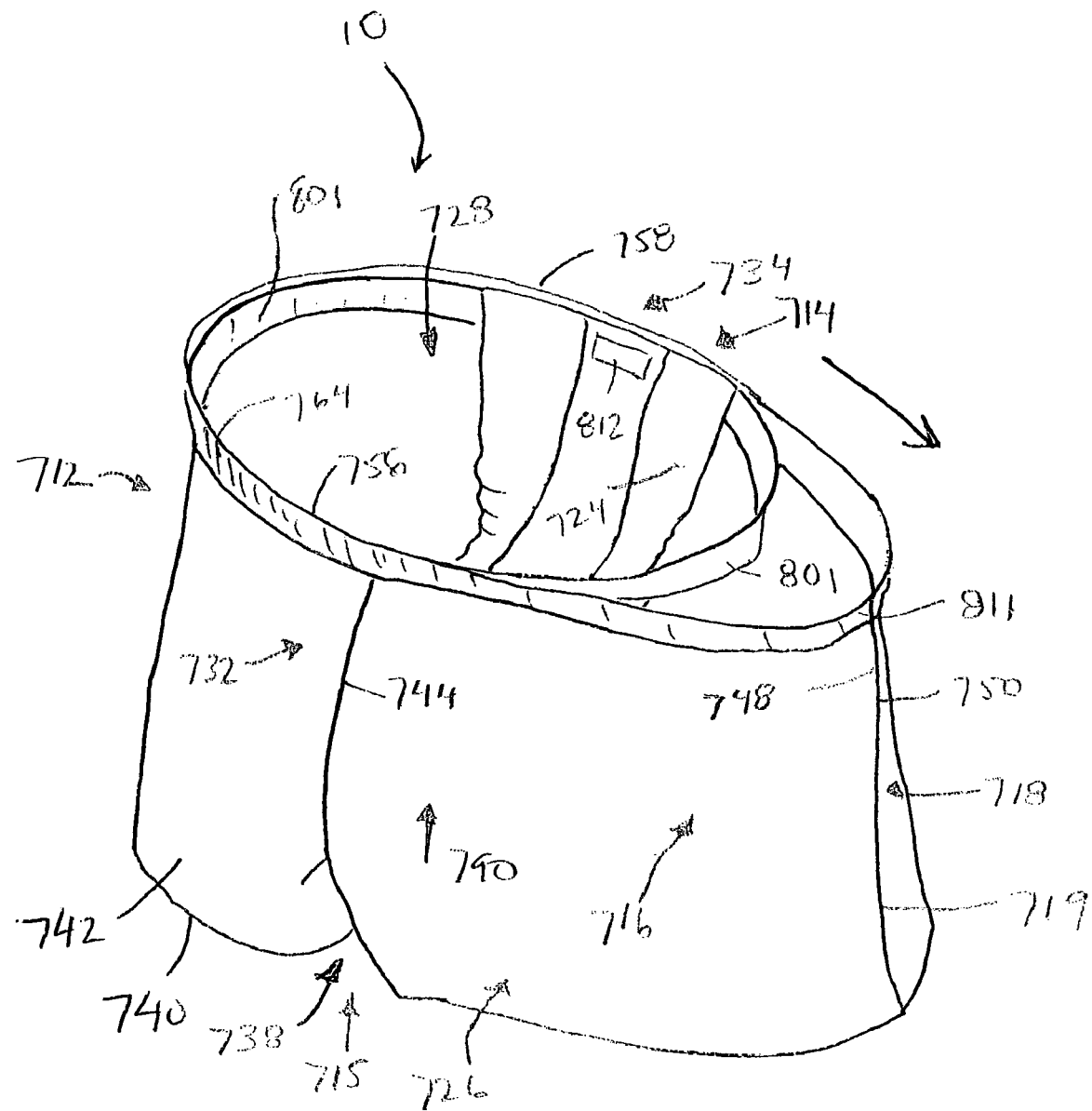
FIG. 12A is a perspective of the absorbent garment of FIG. 12, showing one side of the garment shell in a stretched state and the inner waist band in a non-stretched state.
Figure 13:
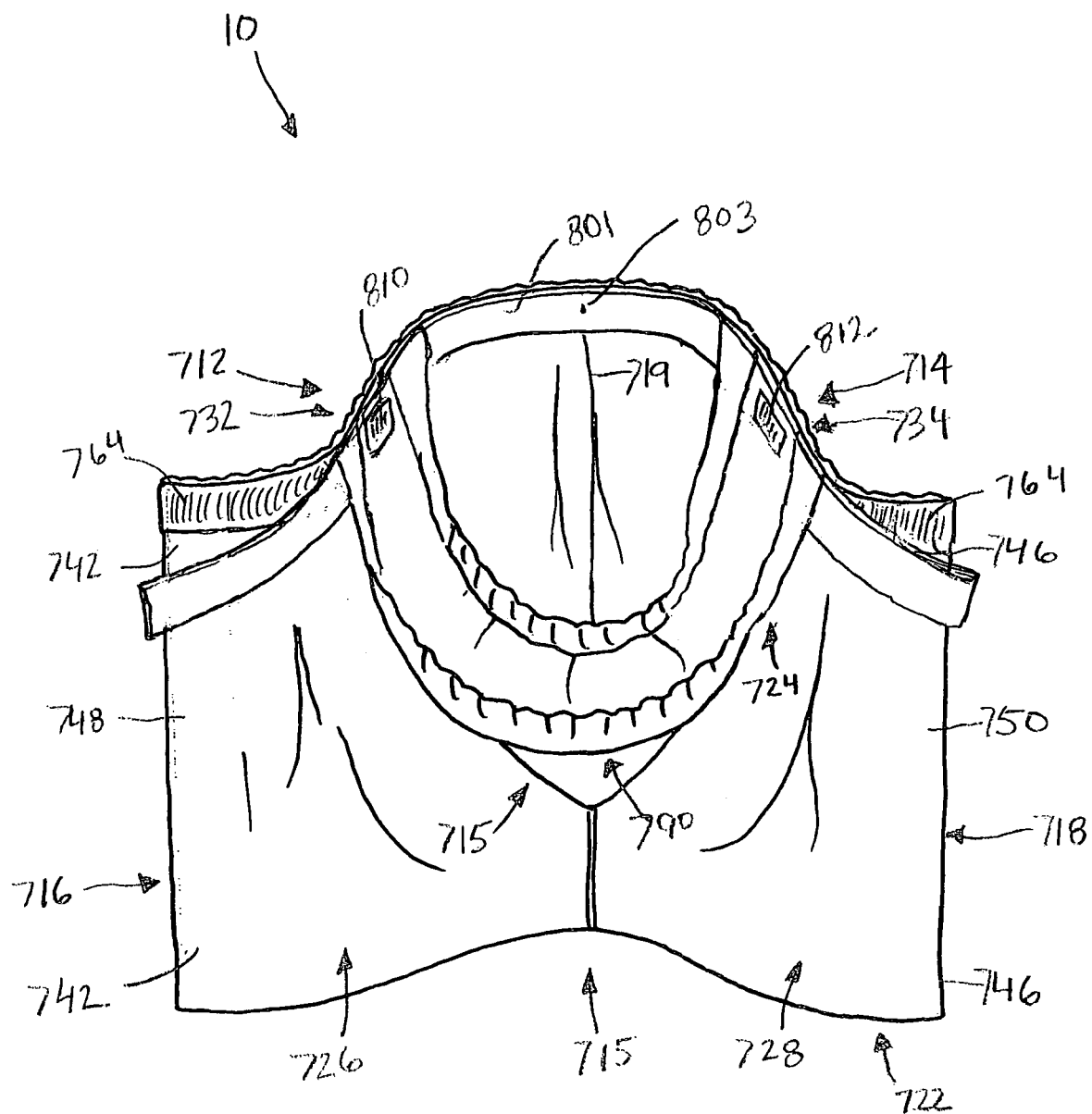
FIG. 13 is a perspective of the absorbent garment of FIG. 12, showing one side of the garment in a disassembled state.

Referring now to the drawings, and in particular to FIGS. 12 and 13, an absorbent garment according to another embodiment of the present invention is indicated in its entirety by the reference numeral 10. In this embodiment, an absorbent assembly 724 may be permanently attached to a garment shell 722 so that the entire absorbent garment is disposable. The absorbent garment 10 is configured to be worn on a wearer's waist and generally has a front waist region, indicated generally at 712, a back waist region, indicated generally at 714 and a crotch region, indicated generally at 715. The front and back waist regions 712, 714 have respective side regions 716, 718 which are attached to each other along side seams 719. As used herein, the term "seam" is intended to refer to a region along which two components are overlapped or otherwise in abutment with each other and may or may not be attached to each other.

With particular reference to FIGS. 12 and 13, the garment shell 722 comprises a front panel assembly, which is generally indicated at 726, having laterally opposite side margins 748 and a back panel assembly, which is generally indicated at 728 in FIG. 12, having laterally opposite side margins 750. As will be described in further detail later herein, the side margins 748, 750 of the front and back panel assemblies 726, 728 of the garment shell 722 are attached to each other to broadly define the side seams 719 of the absorbent garment 10, and to define the three-dimensional configuration of the garment shell during wear.

In its three-dimensional configuration as shown in FIG. 12, the garment shell 722 has a front waist region 732 which at least in part defines the front waist region 712 of the absorbent garment 10, a back waist region 734 which at least in part defines the back waist region 714 of the absorbent garment, and front and back waist ends, designated 756 and 758, respectively, which together generally define the waist opening 736 of the garment shell. In the illustrated embodiment, the garment shell 722 is configured to resemble a pair of shorts and thus further has a crotch region 738 extending longitudinally between and interconnecting the front waist region 732 and the back waist region 734 of the garment shell. The crotch region 738 of the garment shell 722 at least in part defines the crotch region 715 of the absorbent garment 10, and also in part defines leg openings 740 of the garment shell (broadly referred to herein as outer leg openings of the absorbent garment). However, it is understood that the crotch region 738 of the garment shell 722 may be omitted (so that the crotch region 715 of the absorbent garment 10 is defined solely by the absorbent assembly 724 as described later herein), such as where the garment shell is intended to resemble a skirt (in which case only one leg opening 740 of the garment shell is provided to accommodate both legs of the wearer), without departing from the scope of this invention.

The front panel assembly 726 of the garment shell 722 comprises a pair of panel members 742 which are in particular embodiments permanently attached to each other, such as by ultrasonic bonding, pressure bonding, thermal bonding, adhesive bonding, stitching or other conventional attachment technique, along a central seam 744 extending longitudinally from the front waist region 732 to the crotch region 738 of the garment shell. The back panel assembly 728 comprises a pair of panel members 746 configured and permanently attached to each other in a manner similar to the panel members 742 of the front panel assembly 726 along a central seam (not shown) extending longitudinally from the back waist region 734 to the crotch region 738 of the garment shell 722. It is understood, however, that each of the front and back panel assemblies 726, 728 may be constructed of a single panel member (e.g., of unitary construction) without departing from the scope of this invention. Alternatively, the front and back panel members 742, 746 on one side of the garment shell 722 may be formed integrally at the crotch region 738 thereof so that no attachment of the panel members is necessary at the leg openings.

The panel members 742, 746 of the front and back panel assemblies 726, 728 of the garment shell 722 can be constructed of any suitable disposable material, and more suitably a material that provides a generally cloth-like texture. The garment shell is desirably intended to be disposable after a single use. As an example, the panel members 742, 746 may be constructed from natural and/or synthetic sources and may be constructed in any suitable manner including, but not limited, to nonwovens such as spunbond, meltblown, spunbond film laminates, bonded carded web, spunlace, hydroentangled, and needlepunched fabrics. The panel members 742, 746 are suitably liquid permeable, although it is understood that the panel members may be liquid impermeable without departing from the scope of this invention.

The amount of overlap between the side margins 748, 750 of the front and back panel assemblies 726, 728 at the side seams 719 of the garment shell 722 (broadly, the overlap of the side regions 716, 718 of the front and back waist regions 712, 714 of the absorbent garment 10) is suitably in the range of about 0.1 inches (2.5 millimeters (mm)) to about 25.4 mm (1 inch), and more suitably in the range of about 13 (mm) (0.5 inches) down to about 5 mm (0.2 inches). It should be noted that the front and back panel assemblies 726, 728 can overlap at the side seams 719 in a "lap" seam manner, or in a "butt" or "fin" seam manner.

To enhance the appearance of the absorbent garment 10 as well as the fit of the absorbent garment on the wearer's waist, an elastic member 764 (e.g., waistband elastics) can be operatively joined to the front and back panel assemblies 726, 728 generally at the respective waist ends 756, 758 thereof. Desirably, as best seen in FIGS. 12 and 13, the elastic member 764 can be operatively joined to the entire front waist end 756 of the garment shell 722. Likewise, another elastic member 764 can be operatively joined to the back waist end 758. The elastic members 764 can be operatively joined to the garment shell 722 while in a stretched condition so that upon retraction the elastic members gather the garment shell at the front and back waist ends 756, 758 to provide a gathered appearance and to further provide an elastic fit of the absorbent garment on the wearer's waist, and to form a shell waist band 811. The elastic member 764 can be joined to either the outwardly facing surface or the body facing surface of the front and back waist ends 756, 758.

Most desirably, the entire absorbent assembly 724 is "disposable," and constructed from the same materials as absorbent assembly 24, described herein. As such, the various materials and methods for constructing the absorbent assembly 724 are the same as for the absorbent assembly 24 as shown in FIGS. 3 and 3A. In addition, the materials from which the absorbent assembly 724 is made may be stretchable.

Figure 14:
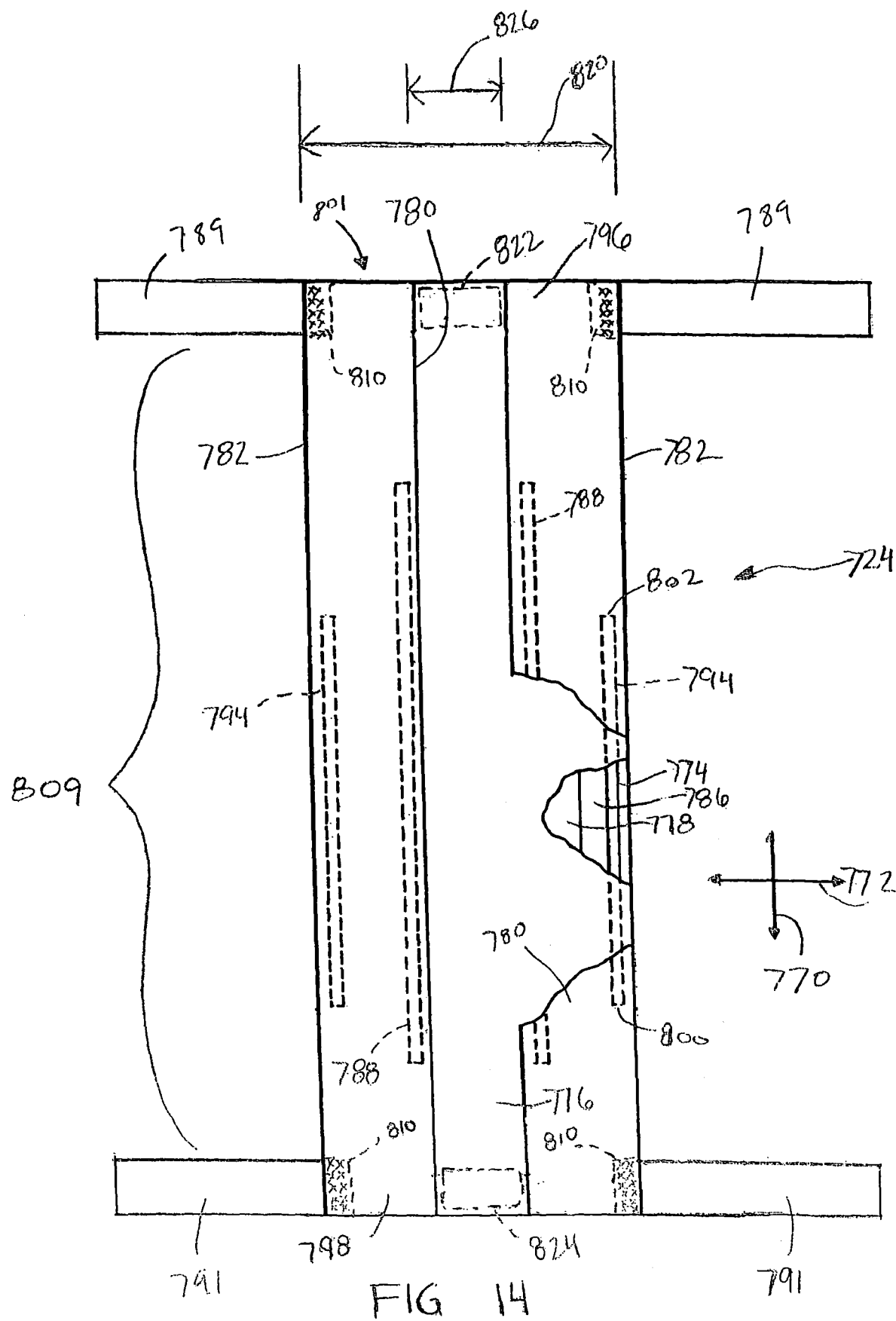
FIG. 14 is a plan view of an absorbent assembly of the absorbent garment of FIG. 12 with the absorbent assembly shown in a partially disassembled (split waistbands), stretched and laid flat condition, and showing the surface of the absorbent assembly that faces the wearer of the absorbent garment, and with portions cut away to show underlying features.
Figure 14A:
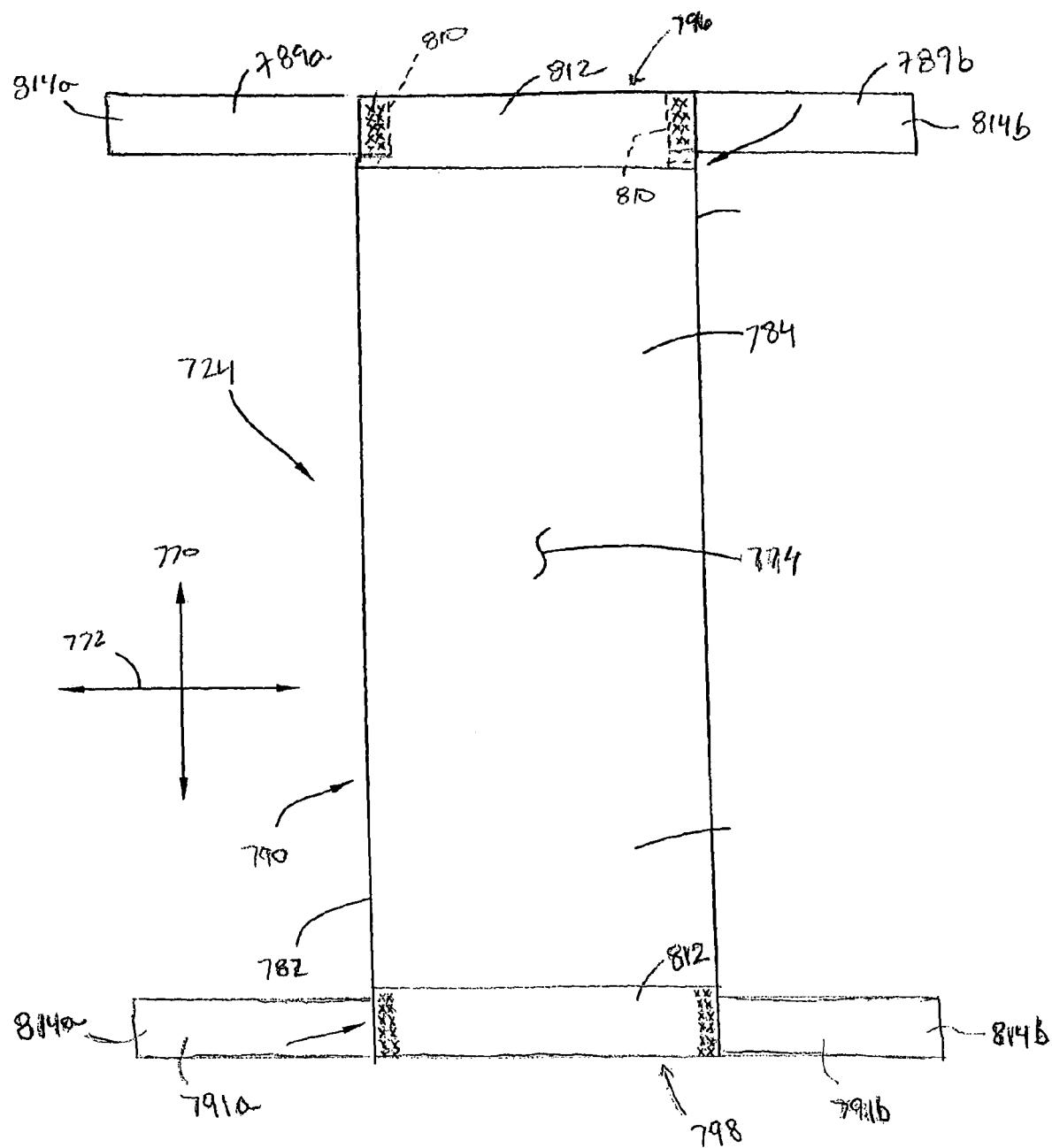
FIG. 14a is a plan view similar to FIG. 4, but showing the surface of the absorbent that faces away from the wearer of the absorbent garment.
Figure 15:
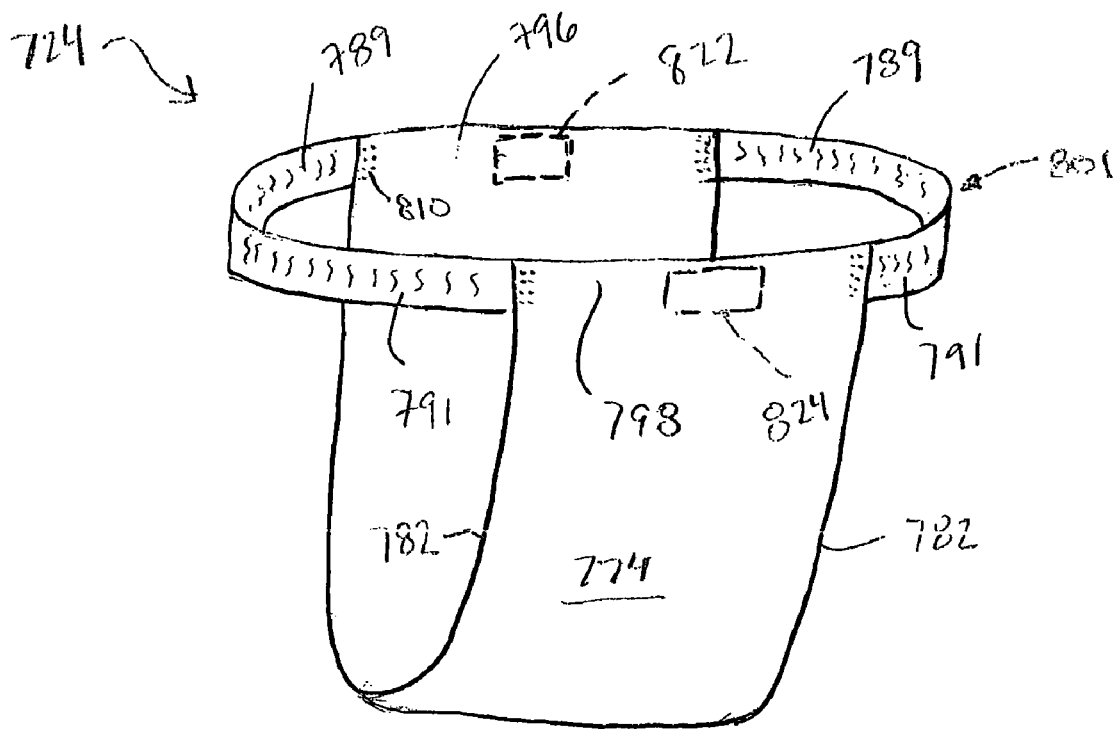
FIG. 15 is a schematic perspective view of the absorbent assembly of FIG. 14.

The absorbent assembly 724, as is illustrated in FIGS. 14 and 14A, is detached from the garment shell 722 and in a laid flat configuration. The absorbent assembly 724 is illustrated as being rectangular in shape, and has a longitudinal axis 770 and a transverse, or lateral axis 772. It is understood that the absorbent assembly 724 may be other than rectangular, such as hourglass-shaped, T-shaped, I-shaped or other suitable shape without departing from the scope of this invention. Further, the absorbent assembly 724 may be configured like a jock-strap. The absorbent assembly 724 comprises an outer cover 774, a bodyside liner 776 in superposed relationship with the outer cover, an absorbent body 778 disposed between the outer cover and the bodyside liner, and a pair of laterally spaced containment flaps 780 configured to inhibit the transverse flow of body exudates on the liner to the side edges 782 of the absorbent assembly. The absorbent assembly 724 further includes a front belt members 789 and back belt member 791.

Figure 17:
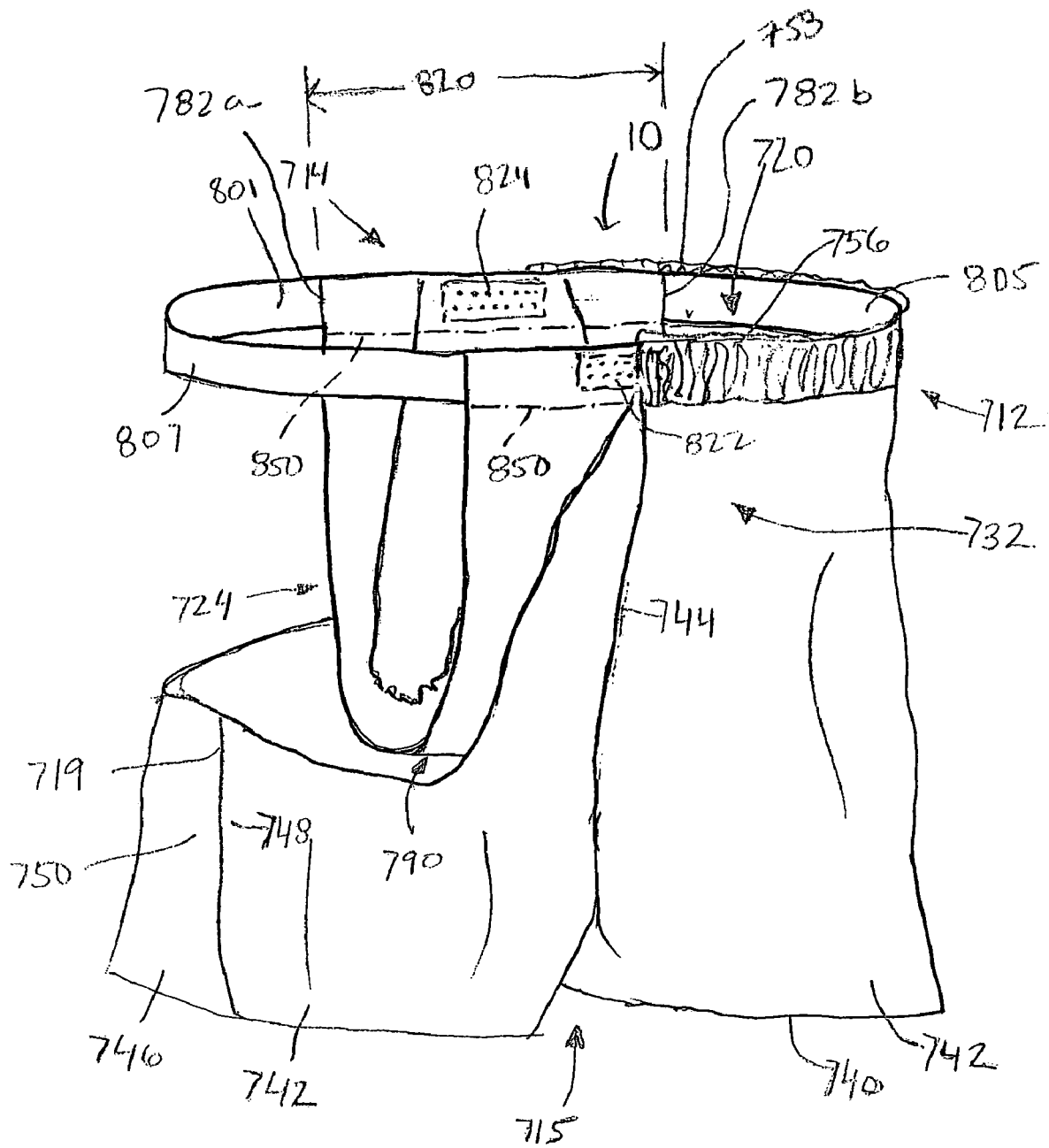
FIG. 17 is a perspective of a ninth embodiment of an absorbent garment of the present invention.

Each belt member 789, 791 of absorbent garment 10 is used to enhance the fit of the absorbent assembly 724 within absorbent garment 10 by forming an inner waist band 801, see FIGS. 12 and 13. More specifically, the belt members 789, 791, once attached to one another and to the absorbent assembly as described herein, are intended to provide tension along the waist ends 796, 798 of the absorbent assembly. This serves to maximize coverage by the absorbent assembly 724 once the absorbent garment 10 is donned by the wearer. As seen in FIG. 17, it is further contemplated that the waist belts could be integrally connected to form a left belt member 805 and a right belt member 807 without departing from the intended scope of the invention. Most desirably, the tension imparted by either belt members 789, 791 or the alternative belt members 805, 807 is greater than the tension imparted by the waist elastics 764 on the garment shell 722. Thus, shell waist band 811 desirably has a tension that is greater than inner waist band 801. The inner waist band 801 need not be flush with or in exact alignment with the shell waist band 811.

The belt members 789, 791 (or 805, 807) are suitably stretchable, and most desirably, suitably elastic. The waist belt material may be constructed from the same as material and exhibit the same properties as the waist belts 274, described herein. Each belt member 789, 791 suitably has a width of at least about 6 mm, and more suitably in the range of about 20 mm to about 80 mm. As an example, the belt members 789, 791 shown in FIGS. 12-17 have a width of approximately 38 mm.

An end portion 810 of each belt member 789, 791 is attached to the absorbent assembly 724 by stitching, adhesive, or by thermal or pressure or ultrasonic bonding, or by other suitable attachment techniques. Suitably, each end portion 810 overlaps a respective waist end 796, 798 of the absorbent assembly by about 3 to 12 mm, or by any length needed to provide enough shear strength to withstand stretching of the inner waistband 801 during use.

In FIG. 14A, belt members 789, 791 have been respectively referred to as waist belts 789a,b and 791a,b for the purpose of discussing how the inner waist band 801 is formed. Specifically, belt member end margins 814a may be permanently attached to one another to join belt members 789a and 791a. Likewise, belt member end margins 814b may be permanently attached to one another to join waist belts 789b and 791b. It should be noted that the respective end margins 814 can overlap in a "lap" seam manner, or in a "butt" or "fin" seam manner. The attachment of the respective end margins 814 may be made by stitching or adhesive, thermal, pressure or ultrasonic bonding, or by other suitable attachment techniques.

As further seen in FIG. 14A, reinforcement panels 812 may be attached to the outer cover 774 of absorbent assembly 724 to reinforce the waist ends 796, 798 and/or to cover the attached end portion 810 of each belt member 789, 791. Desirably, each reinforcement panel 812 is a rectangular piece of non-woven material such as spunbond, spunbond-meltblown-spunbond, BCW, and the like, and is attached to a respective waist end 796, 798 of the absorbent assembly prior to attaching the end portions 810 to the waist ends 796, 798. Desirably, the belt members 789, 791 may be sandwiched between the reinforcement panel 812 and corresponding absorbent assembly waist ends 796, 798.

The outer cover 774 is substantially similar to the outer cover 74 of FIGS. 3 and 3A in that it comprises a multi-layered laminate structure in which at least one of the layers is liquid impermeable. For instance, referring to FIGS. 14 and 14A, the outer cover 774 can include a liquid permeable outer layer 784 and a liquid impermeable inner layer 786 which are suitably joined together by a laminate adhesive, ultrasonic bonds, pressure bonds, thermal bonds, or the like. The inner layer 786 of the outer cover 774 can be both liquid and vapor impermeable, or it may be liquid impermeable and vapor permeable. The inner layer 786 can be manufactured from a thin plastic film, although other flexible liquid impermeable materials may also be used. The suitable thin plastic films as described herein for inner layer 786 may be used.

Alternatively, the outer cover 774 may comprise a single layer of liquid impermeable material. As previously discussed, the liquid impermeable material can permit vapors to escape from the interior of the disposable absorbent article while still preventing liquids from passing through the outer cover 774. For example, the outer cover 774 may be constructed of a microporous polymer film or a nonwoven fabric that has been coated or otherwise treated to impart a desired level of liquid impermeability. The suitable microporous film as described herein for outer cover 74 may be used.

The liquid permeable bodyside liner 776 is illustrated as overlying the outer cover 774 and absorbent body 778, and may but need not have the same dimensions as the outer cover 774. The bodyside liner 776 is desirably compliant, soft feeling, and non-irritating to the wearer's skin. Further, the bodyside liner 776 can be less hydrophilic than the absorbent body 778, to present a relatively dry surface to the wearer and to permit liquid to readily penetrate through the liner. Alternatively, the bodyside liner 776 can be more hydrophilic or can have essentially the same affinity for moisture as the absorbent body 778 to present a relatively wet surface to the wearer to increase the sensation of being wet. This wet sensation can be useful as a training aid. The hydrophilic/hydrophobic properties can be varied across the length, width and depth of the bodyside liner 776 and absorbent body 778 to achieve the desired wetness sensation or leakage performance. The bodyside liner 776 can be manufactured from the same web materials used to manufacture bodyside liner 148, described herein.

The absorbent body 778 (FIG. 14) is positioned between the outer cover 774 and the bodyside liner 776, which can be joined together by any suitable means such as adhesives, ultrasonic bonds, pressure bonds, thermal bonds, or the like. As described above with respect to the absorbent body 150, absorbent body 778 can be any structure as described for absorbent body 78.

Containment flaps 780 are located generally adjacent to the side edges 782 of the absorbent assembly 724, and can extend longitudinally along the entire length of the absorbent assembly 724 as shown in FIG. 14 or only partially along the length of the absorbent assembly. Flap elastic members 788 (FIG. 14) can be operatively joined with the containment flaps 780 in a suitable manner as is well known in the art, such as by adhering the elastic members to the flaps while the elastic members are in a stretched condition so that the flaps are biased by the elastic members to a longitudinally gathered configuration. The elasticized containment flaps 780 can define a partially unattached distal edge (not shown), unattached to the liner 776, which assumes an upright configuration in at least the crotch region 790 of the absorbent assembly 724 during wear to form a seal (e.g., an elastic fit) against the wearer's body. Suitable constructions and arrangements for the containment flaps 780 are generally well known to those skilled in the art, as described above. It is understood, however, that the containment flaps 780 may be omitted without departing from the scope of this invention.

To enhance the fit of the absorbent garment 10 on the wearer and to further inhibit leakage of body exudates, the absorbent assembly has leg elastic members 794 (FIG. 14), as are known to those skilled in the art. The leg elastic members 794 can be operatively joined to the outer cover 774 and/or the bodyside liner 776 and extend longitudinally adjacent the opposite side edges 782 generally through the crotch region 790 of the absorbent assembly 724. Each leg elastic member 794 has, in particular embodiments, a front terminal point 800 and a back terminal point 802, which represent the longitudinal ends of the elastic gathering caused by the leg elastic members.

To further enhance the fit of absorbent garment 10, absorbent assembly 724 it is operatively attached to the garment shell at the front and back waist regions 732 and 734. The operative attachment occurs only at a specific area to prevent the entire end width 820 of the absorbent assembly from gathering or bunching together in the direction of lateral axis 772 (see FIG. 14). Desirably, waist end 796 has a pre-designated region of operative attachment at a front attachment zone 822, and waist end 798 has a pre-designated region of operative attachment at a rear attachment zone 824. As seen in FIG. 14, each attachment zone 822, 824 has a rectangular shape shown in phantom. However, the shape may be other than rectangular, such as hourglass-shaped, oval-shaped I-shaped or any other suitable shape without departing from the scope of this invention.

The width 826 of each attachment zone 822, 824 is such that when the absorbent garment 10 is worn, the absorbent assembly 724 is adequately secure within the garment shell 722, while allowing the absorbent assembly waist ends 796, 798 to adequately spread across the wearer's waist to prevent leakage of exudates. "Adequately secure" means that during use, the absorbent assembly 724 will remain permanently attached to the garment shell 722 at the site of the attachment zones 822, 824. Desirably, the longitudinal axis of the absorbent assembly 724 will be approximately perpendicular to the garment shell waist ends 756, 758 while being worn. Suitably, it is desired that the attachment zones 822, 824 have a zone width 826 that is about 1 percent to about 70 percent of the absorbent assembly width 820. More suitably, it is desired that the attachment zones 822, 824 have a zone width 826 that is about 5 percent to about 60 percent of the absorbent assembly width 820. Even more suitably, it is desired that the attachment zones 822, 824 have a zone width 826 that is about 20 percent to about 50 percent of the absorbent assembly width 820. However, the attachment zones 822, 824 may have a zone width 826 ranges from about 1 percent to about 95 percent of the absorbent assembly width 820.

Within the area defined by the attachment zones 822, 824, the waist ends 796, 798 are respectively and operatively joined to the absorbent assembly 724, such as by attaching the shell waist elastic members 764 to the outer cover 774 and/or the body side liner 776 while the elastic members are in a stretched condition. Upon retraction, the elastic members 764 gather the absorbent assembly at the attachment zones 822, 824. In the illustrated embodiment, the waist ends 796, 798 are operatively joined to the absorbent assembly 724 at attachment zones 822, 824 respectively. Most desirably, as shown in FIGS. 12 and 13, the combination of the front waist belt 789, back waist belt 791, and the operative attachment of the waist elastic members 764 to absorbent assembly 724, together provide an elastic fit of the absorbent garment 10 against substantially the entire waist of the wearer. Further, it is most desirable that inner waist band 801 (the combination of the front waist belt 789, back waist belt 791, and waist ends 796, 798 provides a tension that is greater than the waist elastics 764 of garment shell 722.

The absorbent assembly 724 can also incorporate other materials or components designed primarily to receive, temporarily store, and/or transport liquid along the mutually facing surface with the absorbent body 778, thereby maximizing the absorbent capacity of the absorbent assembly. For example, one suitable additional component is commonly referred to as a surge layer (not shown). As described above, various woven and non-woven fabrics can be used to construct a surge layer.

Figure 16:
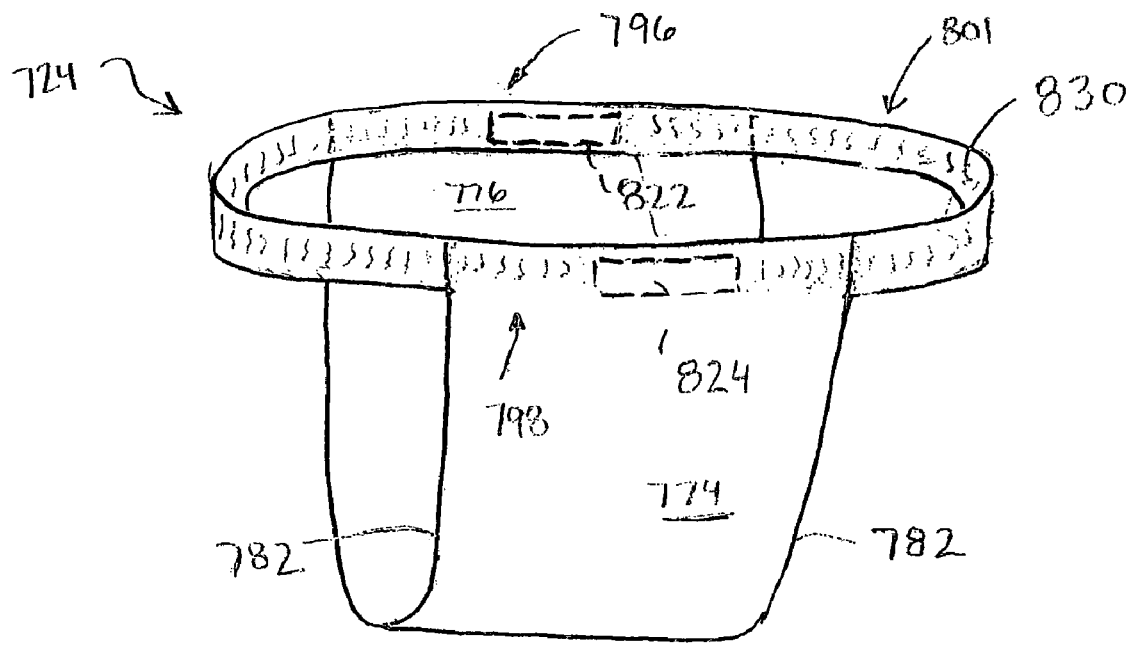
FIG. 16 is a schematic perspective view of an absorbent assembly of an eighth embodiment of the absorbent garment.

In an alternative embodiment of the absorbent assembly as shown in FIG. 16, a single waist belt 830 replaces the belt members 789, 791 of the embodiment shown in FIGS. 12-15. Thus, single waist belt 830 is inner waist band 801. Desirably, as in the previous embodiment, waist belt 830 provides a tension that is greater than the waist elastics 764 of garment shell 722. The operative attachment of waist belt 830 to the waist ends 796 and 798 of the absorbent assembly 724, provides an elastic fit of the absorbent garment 10 against substantially the entire waist of the wearer. Waist belt 830 may be operatively attached to either the liner 776 as shown or the outer cover 774 (not shown).

Still referring to FIG. 16, the attachment zones 822, 824, and the waist ends 796, 798, are respectively and operatively joined such as by attaching the shell waist elastic members 764 to the waist belt 830 and/or the outer cover 774 of the absorbent assembly while the elastic members are in a stretched condition. Upon retraction, the elastic members 764 in conjunction with waist belt 830 gather the absorbent assembly at the attachment zones 822, 824. However, it is further contemplated that in this embodiment, the waist elastics 764 may be omitted where the garment shell 722 is operatively attached to the attachment zones 822, 824, (not shown), leaving only the waist belt 830 to gather the absorbent assembly at the attachment zones.

In an alternative embodiment of the garment 10 as shown in FIG. 17, the absorbent assembly has a stress concentration or line of detachment 850 extending laterally across the width 820 of the absorbent assembly and below the attachment zones 822, 824 and/or below the inner waist band 801. The line of detachment 850 my be made by perforating the absorbent assembly 724 through both the outer cover 774 and liner 776, or by any other appropriate methods such as bonding, cutting, applying a knurled roll, and the like. The line of detachment 850 may be incorporated into the embodiments shown in FIGS. 1-16 and 18. The purpose of having a line of detachment in garment 10 is to provide a way for the wearer to permanently separate the absorbent portion 809 (located between waist ends 796, 798 as seen in FIG. 14) from the garment shell 722. For instance, if the wearer soils the absorbent portion 809 of the absorbent assembly, he or she may tear the absorbent portion 809 away and continue to wear the garment shell 722. Such a situation could arise if the wearer is unable to conveniently access a fresh pair of underwear to wear after an insult occurs, such as in the early hours of the morning.

Figure 18:
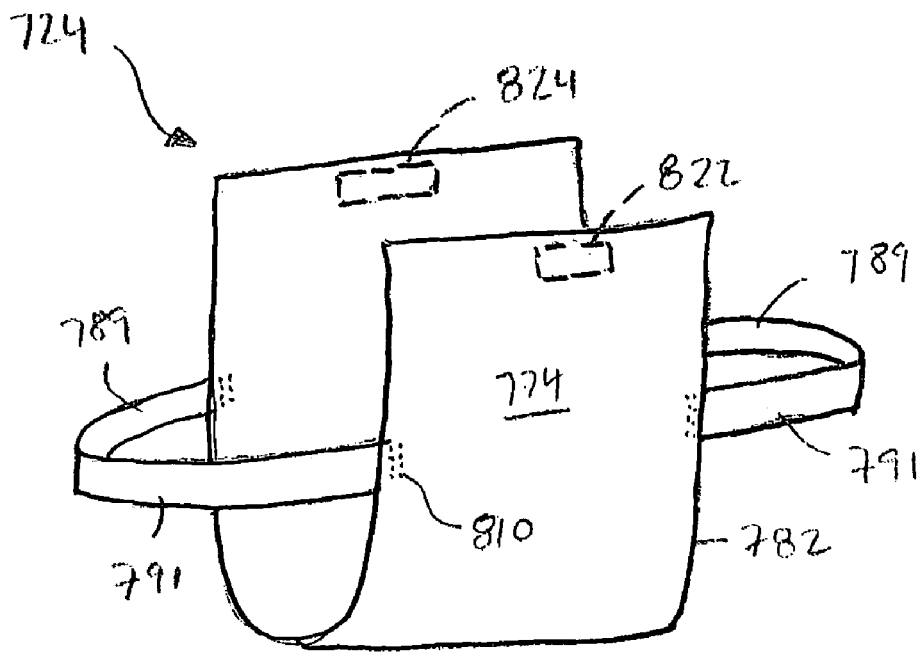
FIG. 18 is a schematic perspective view of an absorbent assembly of a tenth embodiment of the absorbent garment.

The alternative embodiment of the absorbent assembly shown in FIG. 18 is the same at that shown in FIGS. 12-15 except that each belt members 789, 791 (inner bands) are attached to the sides 782 of absorbent assembly 724 at margins 810 so as to provide a close fit of the absorbent garment 10 against the hips of the wearer. Alternatively, as in the embodiment of FIG. 12, belt members 789 and 791 may be substituted with single left and right belt members (not shown).

Figure 19:
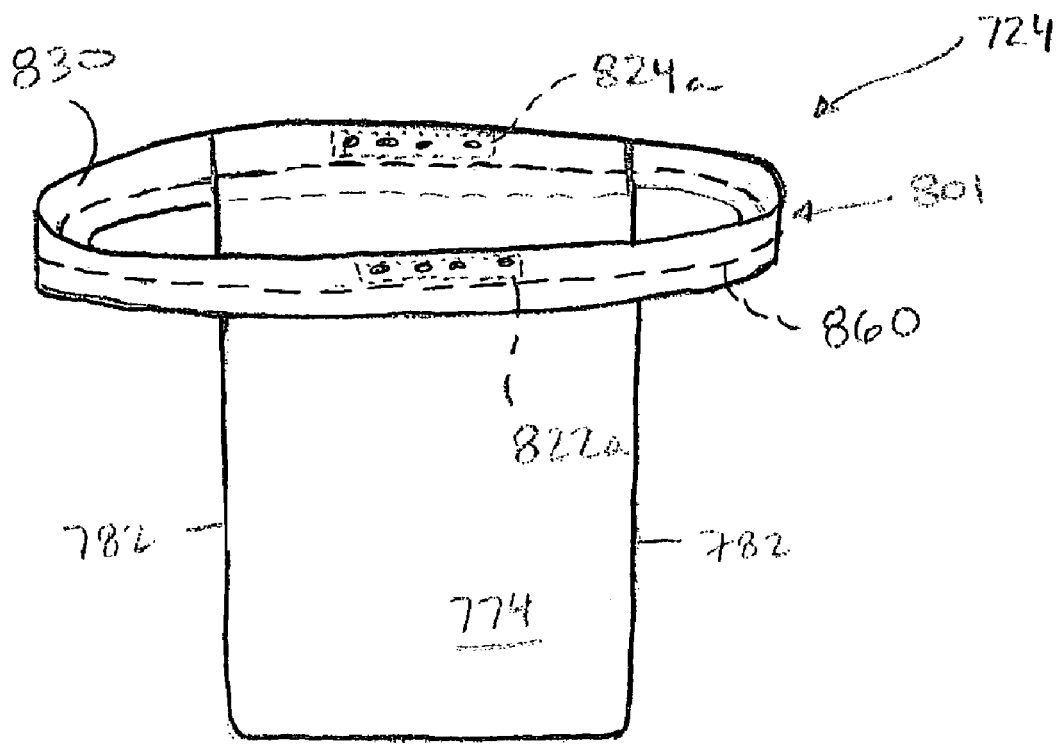
FIG. 19 a schematic perspective view of an absorbent assembly of an eleventh embodiment of the absorbent garment.

A further alternative embodiment of the absorbent assembly 724 as shown in FIG. 19 has a stress concentration or line of detachment 860 around the entire circumference of the inner waist band 801, to provide the wearer with another way to permanently separate the absorbent portion 809 from the garment shell 722. This line of detachment 860 is desirably a line of perforation or other stress concentrators such as bonded areas, cut portions, areas having less adhesive, prestressed or weakened portions, and the like. The line of detachment 860 may be applied to any of the embodiments shown in FIGS. 1-16. Most desirably, the attachment zones are located above the line of detachment 860, such attachment zones referenced as front attachment zone 822*a* and rear attachment zone 824*a*. Further, it is most desirable to apply the circumferential line of detachment 860 to the embodiment of FIG. 16, which has a full waist band 830.

The flap elastic members 788, the waist elastic members 764, leg elastic 774, belt members 789, 791, 805 and 807, and waist belt 830 can be formed of any suitable elastic material. As is well known to those skilled in the art, examples of suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

With respect to the embodiments relating to FIGS. 12-17 and 19, the inner waist band 801 may be tacked to the garment shell 722 for the purpose of keeping the inner waist band 801 somewhat concentric with the shell waist band 811 as the garment is donned, by pulling the garment over the wearer's hips. Further, it is less likely that the wearer will put a leg through the inner waist band 801 and the shell waist band 811 while donning the garment 10. For example, as seen in FIG. 13, as single tack point 803 is located near side seam 719. In addition to or in the alternative, two or more tack points may be used to temporarily attach the inner waist band 801 to the shell waist band 811 at or near side margins 750, 748. Regardless of tack point location, the bonds creating the tack points may be permanently broken by the wearer once the garment is donned. The purpose of breaking such bonds is to allow the absorbent assembly to act more independently of the garment shell 722 for better comfort and less restriction on the absorbent assembly. Tack points 803 may be created with adhesive, pressure or thermal bonds or any other suitable method.

For reasons of simplicity, the various embodiments of the absorbent assembly shown in FIGS. 15, 16, 18 and 19 are depicted schematically. It is intended that the absorbent assembly shown in these figures may include various features such as containment flaps, leg elastics, an outer cover, a liner, an absorbent body, etc. In addition, the width 826 of the front and rear attachment zones may vary as described above in the embodiment of FIG. 12-14.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A disposable absorbent garment for wear about a wearer's waist, said disposable absorbent garment comprising:
    a garment shell configured for encircling the wearers waist and having a front waist region, a front waist end at said front waist region, a back waist region, and a back waist end at said back waist region, the garment shell comprising a front panel assembly having laterally opposite side margins, and a back panel assembly having laterally opposite side margins, the garment shell further having a shell waist band located at the front and back waist end thereof;
    an absorbent assembly disposed within the garment shell and constructed to take in and retain body exudates released by the wearer, the absorbent assembly having a front waist region in juxtaposed relation with the front waist region of the garment shell, a back waist region in opposed relationship with the back waist region of the garment shell, a crotch region extending longitudinally between and interconnecting the front waist region and the back waist region, a front waist end with a front attachment zone and a back waist end with a rear attachment zone, the front attachment zone of the absorbent assembly being permanently attached to the front waist region of the garment shell, and the rear attachment zone of the absorbent assembly being permanently attached to the back waist region of the garment shell;

a first belt and a second belt member, each said first and second belt member extending between each of the laterally opposite outer edges of the absorbent assembly to form an inner waist band;

wherein the absorbent assembly has laterally opposite outer edges defining a width thereof, and the front attachment zone and the rear attachment zone have a width that is about 1 percent to about 70 percent of the width of the absorbent assembly.

2. A disposable absorbent garment as set forth in claim 1 wherein the front attachment zone and the rear attachment zone each have a width that is about 20 percent to about 50 percent of the width of the absorbent assembly.

3. A disposable absorbent garment as set forth in claim 1 further comprising a pair of longitudinal containment flaps, wherein each of the front and rear attachment zones are located between the longitudinal containment flaps.

4. A disposable absorbent garment as set forth in claim 1 wherein the inner waist band is disposed in a substantially concentric position with respect to the shell waist band to provide an elastic fit of the absorbent assembly against the wearer's waist.

5. A disposable absorbent garment as set forth in claim 4 wherein the inner waist band is tacked to the shell waist band at one or more tack points located at about the garment side margins so that the inner waist band maintains a substantially concentric relationship to the shell waist band as the garment is donned by the wearer.

6. A disposable absorbent garment as set forth in claim 1 wherein the absorbent garment has at least one outer leg opening and a pair of inner leg openings separate from the at least one leg opening and disposed within the garment shell, the absorbent assembly at least in part defining said inner leg openings of the absorbent garment, said garment shell defining said at least one outer leg opening of the absorbent garment.

7. A disposable absorbent garment as set forth in claim 6 wherein the absorbent assembly is configured to provide an elastic fit of the absorbent assembly against the wearer's legs at the inner leg openings of the absorbent garment, the garment shell being configured to generally hang loose about the wearer's legs at the at least one outer leg opening of the absorbent garment.

8. A disposable absorbent garment as set forth in claim 1 wherein the elastic tension of the inner waist band is greater than elastic tension of the shell waist band.

9. A disposable absorbent garment as set forth in claim 8 wherein the garment shell has a boxer short configuration.

10. A disposable absorbent garment as set forth in claim 8 wherein the garment shell has a configuration selected from the group comprising pants, skorts, skirts and swim trunks.

11. A disposable absorbent garment as set forth in claim 1 further comprising a line of detachment between the absorbent assembly and the garment shell so that the absorbent assembly can be permanently separated from the garment shell at the line of detachment.

12. A disposable absorbent garment as set forth in claim 1 wherein the absorbent assembly comprises a liquid permeable liner defining the inner surface of the absorbent assembly adapted for contiguous relationship with the wearer, an outer cover in generally opposed relationship with the liner and defining the outer surface of the absorbent assembly, and a disposable absorbent body disposed between the liner and the outer cover.

13. A disposable absorbent garment as set forth in claim 1 wherein the outer cover of the absorbent assembly is liquid impermeable and the garment shell is liquid permeable.

14. A disposable absorbent garment for personal wear about the wearer's waist, said absorbent garment comprising:

a garment shell configured for encircling the wearer's waist, said garment shell having a front waist region, a front waist end at said front waist region, a back waist region, and a back waist end at said back waist region, the absorbent assembly being disposed generally within the garment shell;

a shell waist band comprising at least one elastic member operatively attached to at least the garment shell front waist end or the garment shell back waist end;

an absorbent assembly disposed within the garment shell and constructed to take in and retain body exudates released by the wearer, the absorbent assembly having a front waist region in juxtaposed relation with the front waist region of the garment shell, a back waist region in juxtaposed relation with the back waist region of the garment shell, a crotch region extending longitudinally between and interconnecting the front waist region and the back waist region, a front waist end with a front attachment zone and a back waist end with a rear attachment zone;

an inner waist band for supporting the absorbent assembly around the wearer's waist, the inner waist band attached to the front waist end and the back waist end of the absorbent assembly;

wherein the absorbent assembly has laterally opposite outer edges defining a width thereof and the front attachment zone and the rear attachment zone each have a width that is about 5 percent to about 60 percent of the absorbent assembly width, and wherein the shell waist band is permanently and operatively attached to the inner waist band at the front and rear attachment zones.

15. A disposable absorbent garment as set forth in claim 14 wherein the elastic tension of the inner waist band is greater than elastic tension of the shell waist band.

16. A disposable absorbent garment as set forth in claim 14 wherein the garment shell has a boxer-short configuration.

17. A disposable absorbent garment as set forth in claim 16 further comprising a line of detachment between the absorbent assembly and the garment shell so that the absorbent assembly can be permanently separated from the garment shell at the line of detachment.

18. A disposable absorbent garment for personal wear about the wearer's waist, said absorbent garment comprising:

a garment shell configured for encircling the wearer's waist, said garment shell having a front waist region, a front waist end at said front waist region, a back waist region, and a back waist end at said back waist region, the absorbent assembly being disposed generally within the garment shell;

a shell waist band comprising at least one elastic member operatively attached to at least the garment shell front waist end or the garment shell back waist end;

an absorbent assembly disposed within the garment shell and constructed to take in and retain body exudates released by the wearer, the absorbent assembly having a front waist region in juxtaposed relation with the front waist region of the garment shell, a back waist region in juxtaposed relation with the back waist region of the garment shell, a crotch region extending longitudinally between and interconnecting the front waist region and the back waist region, a front waist end with a front attachment zone and a back waist and with a rear attachment zone;

wherein the absorbent assembly has laterally opposite outer edges defining a width thereof, and wherein front attachment zone and the rear attachment zone each have a width that is about 1 percent to about 95 percent of the absorbent assembly width, an inner band for supporting the absorbent assembly around the wearer's torso, the inner band attached to the laterally opposite outer edges of the absorbent assembly;

wherein the shell waist band is permanently and operatively attached to the absorbent assembly at the front and rear attachment zones;

wherein the absorbent garment has at least one outer leg opening and a pair of inner leg openings separate from the at least one leg opening and disposed within the garment shell, the absorbent assembly at least in part defining said inner leg openings of the absorbent garment, said garment shell defining said at least one outer leg opening of the absorbent garment, and wherein the absorbent assembly is configured to provide an elastic fit of the absorbent assembly against the wearer's legs at the inner leg openings of the absorbent garment, the garment shell being configured to generally hang loose about the wearer's legs at the at least one outer leg opening of the absorbent garment.

19. A disposable absorbent garment as set forth in claim 18 wherein the inner band is disposed below the shell waist band to encircle the wearer's hips, to provide an elastic fit of the absorbent assembly against the wearer's hips.

* * * * *